US010054589B2

(12) United States Patent
Leung et al.

(10) Patent No.: US 10,054,589 B2
(45) Date of Patent: Aug. 21, 2018

(54) METHODS TO IDENTIFY AND TREAT SUBJECTS HAVING CORTICOSTEROID-RESISTANT ASTHMA

(71) Applicant: NATIONAL JEWISH HEALTH, Denver, CO (US)

(72) Inventors: Donald Y. M. Leung, Denver, CO (US); Elena Goleva, Denver, CO (US); Lingbo Li, Denver, CO (US)

(73) Assignee: National Jewish Health, Denver, CO (US)

( * ) Notice: Subject to any disclaimer, the term of this patent is extended or adjusted under 35 U.S.C. 154(b) by 0 days.

(21) Appl. No.: 14/767,434

(22) PCT Filed: Feb. 12, 2014

(86) PCT No.: PCT/US2014/016073
§ 371 (c)(1),
(2) Date: Aug. 12, 2015

(87) PCT Pub. No.: WO2014/127026
PCT Pub. Date: Aug. 21, 2014

(65) Prior Publication Data
US 2015/0377884 A1 Dec. 31, 2015

Related U.S. Application Data

(60) Provisional application No. 61/763,870, filed on Feb. 12, 2013, provisional application No. 61/766,800, filed on Feb. 20, 2013.

(51) Int. Cl.
C12Q 1/48 (2006.01)
G01N 33/573 (2006.01)
C07K 16/40 (2006.01)
C12N 15/113 (2010.01)

(52) U.S. Cl.
CPC .......... *G01N 33/573* (2013.01); *C07K 16/40* (2013.01); *C12N 15/1137* (2013.01); *C12Q 1/485* (2013.01); *C07K 2317/76* (2013.01); *C12N 2310/14* (2013.01); *C12N 2320/30* (2013.01); *G01N 2333/91205* (2013.01); *G01N 2333/91215* (2013.01); *G01N 2800/122* (2013.01); *G01N 2800/52* (2013.01); *G01N 2800/7095* (2013.01)

(58) Field of Classification Search
CPC ......... G01N 2800/52; G01N 2800/152; G01N 2333/91205; G01N 2333/91215; G01N 2800/7095; C07K 2317/76; C12N 2320/30; C12Q 1/485
See application file for complete search history.

(56) References Cited

U.S. PATENT DOCUMENTS

2012/0014986 A1 1/2012 Jensen
2012/0077206 A1 3/2012 Metzger et al.
2013/0281405 A1* 10/2013 Lichtenberger ...... A61K 9/0078
514/77

FOREIGN PATENT DOCUMENTS

WO   WO 2011/094598   8/2011

OTHER PUBLICATIONS

Bhattacharyya, S, et al. TAK1 targeting by glucocorticoids determines JNK and IkB regulation in Toll-like receptor-stimulated macrophages. Blood, 2010, vol. 115, No. 10, p. 1921-1931.*
Leung, D.Y.M, et al. Update on glucocorticoid action and resistance. J. Allergy Clin. Immunol., 2003, vol. 111, p. 3-22.*
Badenoch et al. "A Rat Model of Bacterial Keratitis Effect of Antibiotics and Corticosteroid," Archives of Ophthalmology, May 1985, vol. 103, No. 5, pp. 718-722 (Abstract).
Baker et al. "Molecular Structures That Influence the Immunomodulatory Properties of the Lipid A and Inner Core Region Oligosaccharides of Bacterial Lipopolysaccharides," Infection and Immunity, Jun. 1994, vol. 62, No. 6, pp. 2257-2269.
Beck et al. "Glucocorticoids and mitogen- and stress-activated protein kinase 1 inhibitors: Possible partners in the combat against inflammation," Biochemical Pharmacology, Apr. 2009, vol. 77, No. 7, pp. 1194-1205.
Beck et al. "Altered subcellular distribution of MSK1 induced by glucocorticoids contributes to NF-kB inhibition," The EMBO Journal, 2008, vol. 27, No. 12, pp. 1682-1693.
Bhavsar et al. "Effect of p38 MAPK inhibition on corticosteroid suppression of cytokine release in severe asthma," European Respiratory Journal, Apr. 2010, vol. 35, No. 4, pp. 750-756.
Chung "p38 Mitogen-Activated Protein Kinase Pathways in Asthma and COPD," Chest, Jun. 2011, vol. 139, No. 6, pp. 1470-1479.
Deak et al. "Mitogen- and stress-activated protein kinase-1 (MSK1) is directly activated by MAPK and SAPK2/p38, and may mediate activation of CREB," The EMBO Journal, 1998, vol. 17, No. 15, pp. 4426-4441.
Goleva et al. "Corticosteroid-resistant asthma is associated with classical antimicrobial activation of airway macrophages," The Journal of Allergy and Clinical Immunology, Sep. 2008, vol. 122, No. 3, pp. 550-559.
Goleva et al. "IFN-gamma Reverses IL-2- and IL-4-Mediated T-Cell Steroid Resistance," American Journal of Respiratory Cell and Molecular Biology, Feb. 2009, vol. 40, No. 2, pp. 223-230.
Hilty et al. "Disordered Microbial Communities in Asthmatic Airways," PLOS ONE, Jan. 2010, vol. 5, No. 1, e8578, 10 pages.
Huang et al. "Airway microbiota and bronchial hyperresponsiveness in patients with suboptimally controlled asthma," The Journal of Allergy and Clinical Immunology, Feb. 2011, vol. 127, No. 2, pp. 372-381.
Larsen et al. "Divergent Pro-Inflammatory Profile of Human Dendritic Cells in Response to Commensal and Pathogenic Bacteria Associated with the Airway Microbiota," PLOS ONE, Feb. 2012, vol. 7, No. 2, e31976, 11 pages.
Li et al. "Superantigen-induced corticosteroid resistance of human T cells occurs through activation of the mitogen-activated protein kinase kinase/extracellular signal-regulated kinase (MEK-ERK) pathway," The Journal of Allergy and Clinical Immunology, Nov. 2004, vol. 114, No. 5, pp. 1059-1069.

(Continued)

Primary Examiner — Robert S Landsman
Assistant Examiner — Bruce D. Hissong
(74) Attorney, Agent, or Firm — Sheridan Ross P.C.

(57) ABSTRACT

The present invention is directed toward novel methods to identify as well as to treat a subject having an inflammatory disease resistant to corticosteroids.

7 Claims, 28 Drawing Sheets

(56) References Cited

OTHER PUBLICATIONS

Liu et al. "Establishment of Extracellular Signal-Regulated Kinase ½ Bistability and Sustained Activation through Sprouty 2 and Its Relevance for Epithelial Function," Molecular and Cellular Biology, Apr. 2010, vol. 3, No. 7, pp. 1783-1799.
Liu et al. "Cell-specific activation profile of extracellular signal-regulated kinase ½, Jun N-terminal kinase, and p38 mitogen-activated protein kinases in asthmatic airways," The Journal of Allergy and Clinical Immunology, Apr. 2008, vol. 121, No. 4, pp. 893-902.
Miller et al. "LPS, TLR4 and Infectious Disease Diversity," Nature Reviews Microbiology, Jan. 2005, vol. 3, No. 1, pp. 36-46.
Shan et al. "Thymic Stromal Lymphopoietin Receptor-Mediated IL-6 and CC/CXC Chemokines Expression in Human Airway Smooth Muscle Cells: Role of MAPKs (ERK½, p38, and JNK) and STAT3 Pathways," The Journal of Immunology, Jun. 2010, vol. 184, No. 12, pp. 7134-7143.
Yang et al. "Pathogenesis of Steroid-Resistant Airway Hyper-responsiveness: Interaction between IFN- and TLR4/MyD88 Pathways," The Journal of Immunology, Apr. 2009, vol. 182, No. 8, pp. 5107-5115.
International Search Report and Written Opinion for International (PCT) Patent Application No. PCT/US14/16073, dated Jul. 24, 2014 13 pages.
International Preliminary Report on Patentability for International (PCT) Patent Application No. PCT/US2014/016073, dated Aug. 27, 2015 10 pages.

\* cited by examiner

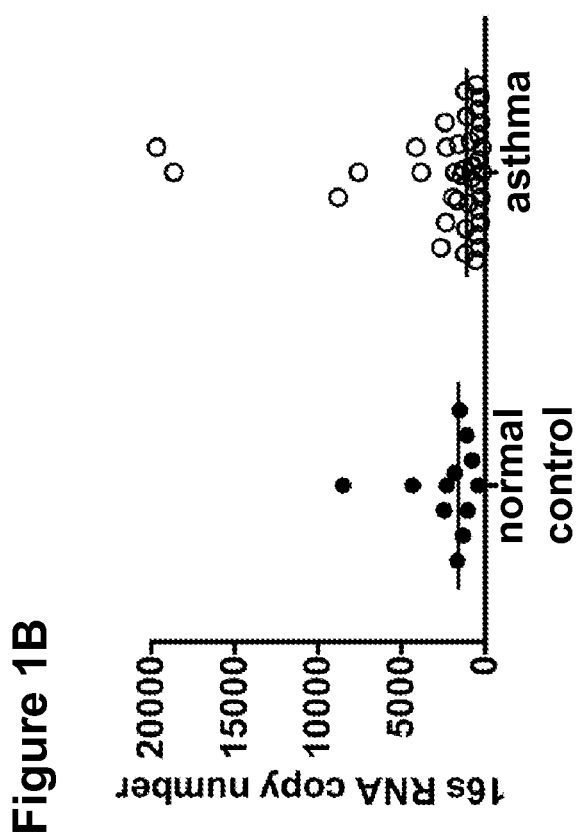

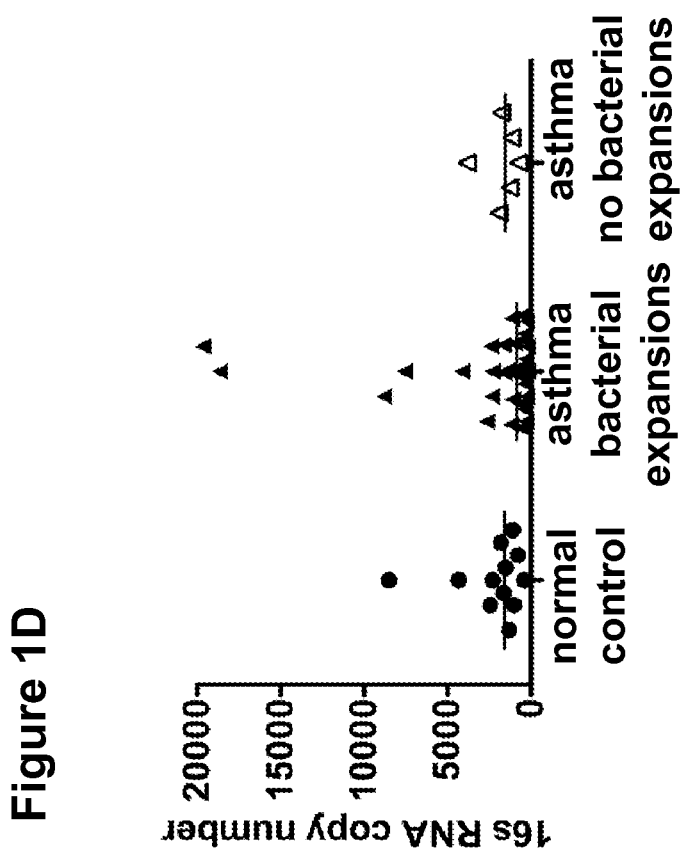

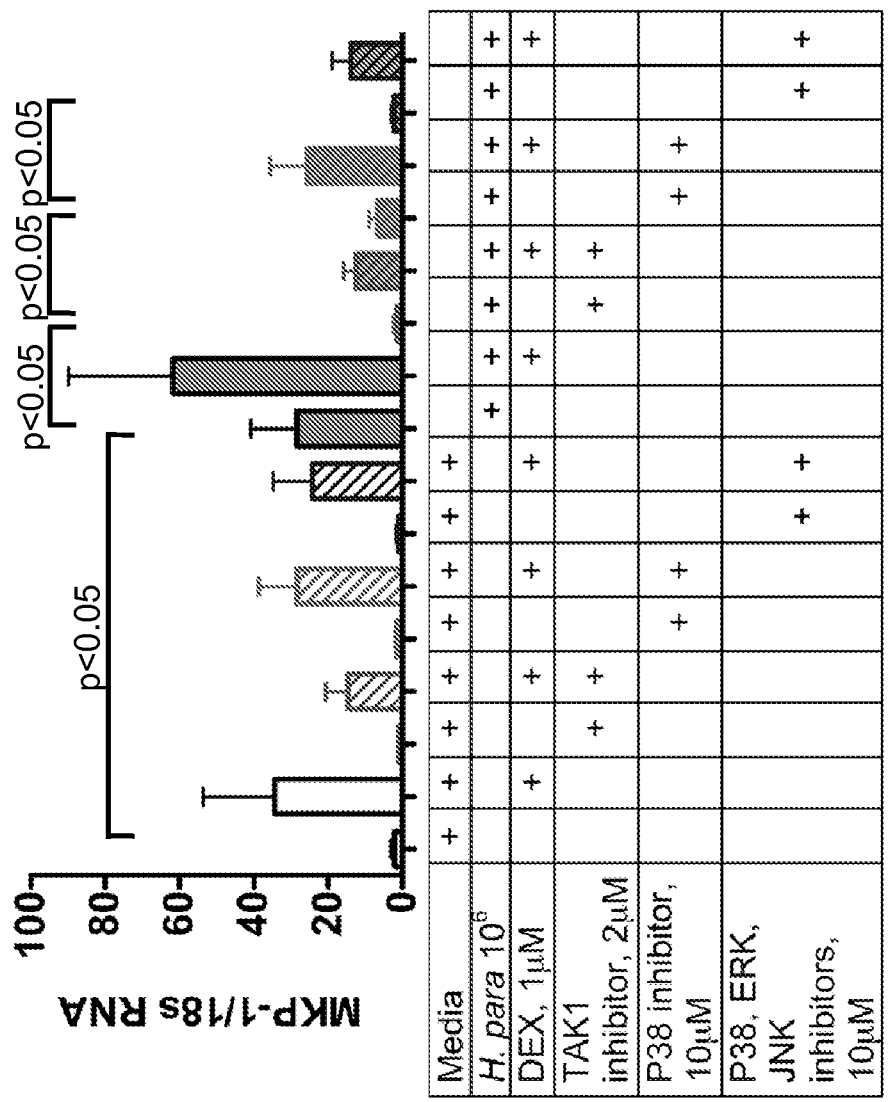

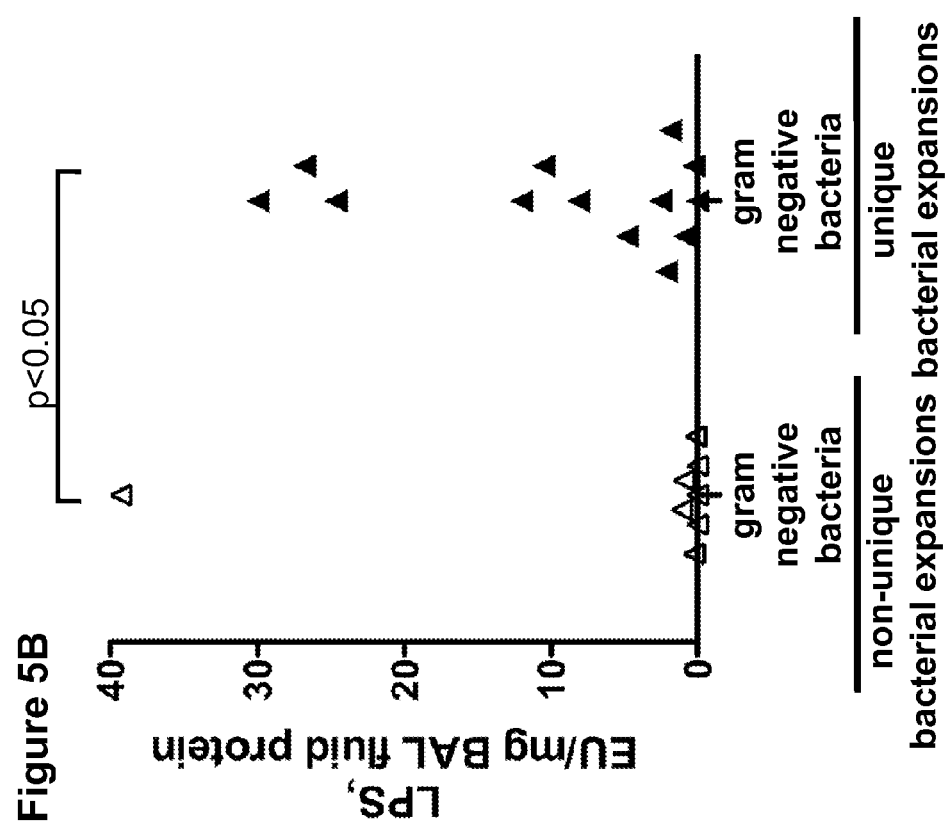

METHODS TO IDENTIFY AND TREAT SUBJECTS HAVING CORTICOSTEROID-RESISTANT ASTHMA

CROSS-REFERENCE TO RELATED APPLICATIONS

This application is a national stage application under 35 U.S.C. 371 of PCT Application No. PCT/US2014/016073 having an international filing date of Feb. 12, 2014, which designated the United States, which PCT application claimed the benefit of priority under 35 U.S.C. 119(e) to U.S. Provisional Patent Application No. 61/763,870, filed Feb. 12, 2013 and to U.S. Provisional Patent Application No. 61/766,800, filed Feb. 20, 2013, all of which are incorporated herein by reference in their entirety.

GOVERNMENT SUPPORT

This invention was made with government support under R01 AI070140, R56 AI070140, and R37 HL037260 awarded by the National Institute of Allergy and Infectious Diseases and the National Heart, Lung, and Blood Institute of the National Institutes of Health. The government has certain rights in the invention.

FIELD OF THE INVENTION

The present invention is directed toward novel methods to identify and treat subjects having an inflammatory disease resistant to corticosteroids.

BACKGROUND OF THE INVENTION

Asthma is associated with variable responses to corticosteroids. There have been no functional studies analyzing airway microbiome effects on corticosteroid responsiveness in asthmatics. National and international guidelines (NIH publication no 07-4051. Bethesda, Md.: National Institutes of Health National Heart Lung and Blood Institute; 2007; Global strategy for asthma management and prevention 2009 (update): Global Initiative for Asthma; 2009) recommend the use of corticosteroids to control airway inflammation in persistent asthma Clinical studies, however, demonstrate highly variable responses to corticosteroid therapy with up to 45% of patients not having a clinical or physiologic response to inhaled corticosteroids (ICS) (Malmstrom K et al., *Ann Intern Med* 1999; 130:487-95; Martin R J et al., *J Allergy Clin Immunol* 2007; 119:73-80; Barnes P J et al., *Lancet* 2009; 373:1905-17), and up to 25% of patients not responding to oral corticosteroids (Leung D Y et al., *J Allergy Clin Immunol* 2003; 111:3-22; quiz 3). These corticosteroid resistant (CR) patients have increased airway inflammation (Leung D Y et al., *J Allergy Clin Immunol* 2003; 111:3-22; quiz 3; Leung D Y et al., *J Exp Med* 1995; 181:33-40) despite treatment with oral steroids, and airway remodeling (Goleva E et al., *J Allergy Clin Immunol* 2007; 120:1065-72) contributing to the severity of asthma. Given variable responses to corticosteroid therapy in asthmatics, alternative therapeutics targeting disease causality are needed for personalized treatment of asthma (Drazen J M., *J Allergy Clin Immunol* 2012; 129:1200-1).

Glucocorticoids (GCs) are the most potent anti-inflammatory drugs used for treatment of asthma and other chronic inflammatory or autoimmune diseases. Up to 20% of asthmatics remain refractory to CS or glucocorticoid (GC) therapy—these patients are referred to as steroid resistant (SR) or steroid insensitive asthmatics (McManus R., *J Endocrinol* 2003; 178:1-4). SR asthmatics are characterized by increased airway inflammation that cannot be inhibited by CS treatment. The role of race, smoking, obesity, vitamin D level, allergens, and infection in steroid resistance is under active investigation (Leung D Y et al., *J Allergy Clin Immunol* 2003; 111:3-22; quiz 23; Althuis M D et al., *J Asthma* 1999; 36:257-264; Sutherland E R et al., *Am J Respir Crit Care Med* 2010; 181:699-704). In addition, endotoxin exposure has recently been identified as an important factor that alters cellular response to CS (Yang M et al., *J Immunol* 2009; 182:5107-5115; Goleva E et al., *J Allergy Clin Immunol* 2008; 122:550-559 e553; Bhaysar P et al., *Thorax* 2008; 63:784-790).

Endotoxin or lipopolysaccharide (LPS), a component of the outer membrane of Gram-negative bacteria, has been implicated in innate immune responses by inducing activation and release of proinflammatory cytokines, nitric oxide, reactive oxygen species and other cell mediators from monocytes and macrophages (Rossol M et al., *Crit Rev Immunol* 2011; 31:379-446). Exposure to endotoxin has been associated with asthma exacerbation (Liu A H., *Paediatr Respir Rev* 2004; 5 Suppl A:S65-71). Several studies have demonstrated that higher exposure to house dust endotoxin is related to asthma severity (Michel 0 et al., *Am J Respir Crit Care Med* 1996; 154:1641-1646; Rizzo M C et al., *Pediatr Allergy Immunol* 1997; 8:121-126P). Previous studies also indicate that exposure of monocytes to LPS induces cellular steroid resistance (Goleva E et al., *J Allergy Clin Immunol* 2008; 122:550-559 e553).

Mammalian cells respond to LPS stimulation through a series of protein interactions, including engagement of LPS binding protein (LBP), CD14, and Toll-like receptor (TLR) 4 (Gioannini T L, et al. *J Biol Chem* 2007; 282:7877-7884), its cell membrane receptor. Intracellular signaling mediated by LPS/TLR4 involves binding of a series of adaptor molecules, including TRIF, TRAM, TIRAP, BTK and MyD88, and leads to sequential kinase phosphorylation (Fitzgerald K A et al., *J Exp Med* 2003; 198:1043-1055). Mitogen activated protein kinases (MAPK)s are the final kinases in this cascade and include p38 MAPK (p38), p42/44 MAPK (ERK) and c-Jun $NH_2$-terminal kinase (JNK) (Guha M, Mackman. *Cell Signal* 2001; 13:85-94). Stimulation of human monocytes with LPS has been shown to result in the phosphorylation and activation of p38, ERK and JNK (Carter A B et al., *Am J Respir Cell Mol Biol* 1999; 20:751-758; Lim W et al., *J Immunol* 2005; 175:5690-5700). Several studies have demonstrated that MAPK pathways are involved in activation of transcription factors, such as NF-κB and AP-1 (Rawadi G et al., *J Immunol* 1999; 162:2193-2203; Oeckinghaus A et al., *Nat Immunol* 2011; 12:695-708); these transcription factors play a critical role in LPS-induced expression of proinflammatory genes, such as TNF-α, IL-10, IL-6, IL-8, MCP-1, E-selectin, VCAM-1 and ICAM-1.

Cytoplasmic glucocorticoid receptor (GCR) mediates cellular response to GCs. Activated GCR translocates to the cell nuclei and acts as a transcriptional factor. GCR can inhibit pro-inflammatory MAPK signaling by inducing nuclear mitogen activated kinase phosphatase (MKP1) expression (Liu Y et al., *Nat Rev Immunol* 2007; 7:202-212; Lasa M et al., *Mol Cell Biol* 2002; 22:7802-7811). At the same time, GCR activity is subject to kinase modulation, activated MAPKs can inhibit GCR function via phosphorylation that will inhibit GCR nuclear translocation in response to GC treatment, cause the GCR to return to the cytoplasm or modify GCR transcriptional activity (Ismaili N et al., *Ann N*

*Y Acad Sci* 2004; 1024:86-101; Galliher-Beckley A J et al., *IUBMB Life* 2009; 61:979-986).

In addition, 16s rRNA gene sequence analysis of the airway microbiota has demonstrated diversified microbial communities in the airways of asthmatics (Hilty M et al., *PLoS One* 2010; 5:e8578; Huang Y J et al., *J Allergy Clin Immunol* 2011; 127:372-81 e1-3). Patients with asthma showed significantly higher bacterial diversity due to expansion of pathogenic bacteria and greater bacterial burden compared with healthy controls. Moreover, airway microbiome composition and greater bacterial diversity significantly correlates with bronchial hyperresponsiveness, including the relative abundance of bacterial families within Proteobacteria. The functional impact of airway microbiome and its contribution to pathophysiologic processes in asthma were not previously known.

SUMMARY OF THE INVENTION

One embodiment of the invention relates to a method to identify a subject having an inflammatory disease resistant to corticosteroid treatment comprising detecting the expansion of one or more gram-negative bacteria in a biological sample from the subject.

In another embodiment, the invention relates to method to identify a subject having an inflammatory disease resistant to corticosteroid treatment comprising detecting the expression of transforming growth factor beta associated kinase-1 (TAK1) in a biological sample from the subject, wherein increased expression of TAK1 compared to a control identifies the subject as having an inflammatory disease resistant to corticosteroid treatment.

In another embodiment, the invention relates to a method to identify a subject having an inflammatory disease resistant to corticosteroid treatment comprising determining the level of phosphorylated TAK1 (p-TAK1) in a biological sample from the subject, wherein an elevated level of p-TAK1 compared to a control identifies the subject as having an inflammatory disease resistant to corticosteroid treatment.

Another embodiment of the invention relates to a method of treating a subject having an inflammatory disease resistant to corticosteroid treatment by administering to the subject a compound that inhibits transforming growth factor beta associated kinase-1 (TAK1) activity.

Another embodiment of the invention relates to a method for diagnosing and treating an inflammatory disease resistant to corticosteroid treatment in a subject comprising analyzing a subject sample for the presence of p-TAK1, wherein the subject is diagnosed as having an inflammatory disease resistant to corticosteroid treatment if the p-TAK1 level is elevated compared to a control p-TAK1 level, and administering a compound that inhibits TAK1 activity to the diagnosed subject.

In one aspect, the compound that inhibits TAK1 activity is a TAK1 inhibitor. In another aspect, the TAK1 inhibitor is selected from a small-molecule inhibitor, a chemical inhibitor, an antibody, a TAK1 siRNA and combinations thereof. In another aspect, the compound is a non-steroidal anti-inflammatory drug.

Another embodiment of the invention relates to a method to predict the response of a subject to corticosteroid treatment, who has, or is at risk of developing an inflammatory disease resistant to corticosteroid treatment, comprising obtaining a biological sample from the subject; and analyzing in the biological sample for the expansion of at least one gram-negative bacteria, wherein the expansion of the of at least one gram-negative bacteria compared to a control predicts the subject to be resistant to corticosteroid treatment.

In another embodiment, the invention relates to a method to predict the response of a subject to corticosteroid treatment, who has, or is at risk of developing an inflammatory disease resistant to corticosteroid treatment, comprising obtaining a biological sample from the subject; and analyzing in the biological sample for the activity of TAK1, wherein an increase or decrease in TAK1 activity compared to a control predicts the subject to be resistant to corticosteroid treatment.

Another embodiment of the invention relates to a TAK1 inhibitor for use in the treatment of an inflammatory disease resistant to corticosteroid treatment in a subject with p-TAK1 levels that are elevated as compared to a control p-TAK1 level.

In another embodiment, the invention relates to a TAK1 inhibitor for use in treating an inflammatory disease resistant to corticosteroid treatment in a subject, comprising analyzing a biological sample from a subject selected from serum, plasma, blood, urine, sputum, peripheral blood mononuclear cells (PBMCs), epithelial cells, sinus tissue, nasal tissue, skin biopsy and bowel biopsy; determining if the subject has elevated p-TAK1 levels as compared to a control; and administering a therapeutically effective amount of an TAK1 inhibitor to the subject if an elevated p-TAK1 level is present.

In one aspect of the above methods of the present invention, the inflammatory disease is selected from an inflammatory lung disease, inflammatory bowel disease, allergic rhinitis, sinusitis and gram negative sepsis. In still another aspect, the inflammatory lung disease is associated with a chronic obstructive disease of the airways. In yet another aspect, the inflammatory lung disease is associated with viral induced inflammation. In yet another aspect, the inflammatory lung disease is triggered by the subject's exposure to environmental conditions selected from second hand smoke, primary tobacco smoke, and an allergen. In another aspect, the inflammatory lung disease is asthma.

In another aspect of the methods of the present invention, the step of determining the expansion of one or more gram-negative bacteria in a biological sample from the subject indentifies the subject as having an inflammatory disease resistant to corticosteroid treatment.

In still other aspects of the methods of the present invention, the gram-negative bacteria is a gram negative bacteria with a Lipid A chain length of 14 carbons or less. In another aspect, the gram-negative bacteria is selected from *Tropheryma, Leptotrichia, Neisseria, Simonsiella, Haemophilus*, and *Campylobacter*.

In yet another aspect of the methods of the present invention, the biological sample is selected from serum, plasma, blood, urine, sputum, peripheral blood mononuclear cells (PBMCs), epithelial cells, sinus tissue, nasal tissue, skin biopsy and bowel biopsy.

In still various aspects, the subject is being administered a non-steroidal anti-inflammatory drug.

In still another aspect of the above methods of the present invention, the step of administering can be by injection, oral administration or inhalation.

One embodiment of the invention relates to a method to identify a subject having an inflammatory disease resistant to corticosteroid (CS) treatment by determining the level of phosphorylated MSK1 (p-MSK1) in a biological sample from the subject. In one aspect, the step of determining the subject's p-MSK1 level comprises determining the subject's p-MSK1 level, wherein an elevated level in the subject as compared to a control p-MSK1 level identifies the subject as having an inflammatory disease resistant to corticosteroid treatment.

Another embodiment of the invention relates to a method of treating a subject having an inflammatory disease resistant to CS treatment by administering to the subject a compound that inhibits MSK1 activity.

Another embodiment of the invention relates to a method for diagnosing and treating an inflammatory disease resistant to corticosteroid treatment in a subject comprising analyzing a subject sample for the presence of p-MSK1, wherein the subject is diagnosed as having an inflammatory disease resistant to corticosteroid treatment if the p-MSK1 level is elevated compared to a control p-MSK1 level, and administering a compound that inhibits MSK1 activity to the diagnosed subject.

In one aspect, the compound that inhibits MSK1 activity is an MSK1 inhibitor. In yet another aspect, the MSK1 inhibitor is selected from a small molecule inhibitor, a chemical inhibitor, an antibody, a MSK1 siRNA and combinations thereof. In still another aspect the compound can be a non-steroidal anti-inflammatory drug.

Another embodiment of the invention relates to a method to predict the response of a subject to CS treatment, who has, or is at risk of developing an inflammatory disease resistant to CS treatment, comprising obtaining a biological sample from the subject, analyzing in the biological sample for at least one marker selected from an elevated level of p-MSK1 or an elevated level of phosphorylated p-38 and wherein an elevated level of at least one marker compared to a control predicts the subject to be resistant to corticosteroid treatment. In one aspect, the marker is an elevated level of p-MSK1.

Another embodiment of the invention relates to a MSK1 inhibitor for use in the treatment of an inflammatory disease resistant to corticosteroid treatment in a subject with p-MKS1 levels that are elevated as compared to a control p-MSK1 level.

Another embodiment of the invention relates to a MSK1 inhibitor for use in treating an inflammatory disease resistant to corticosteroid treatment in a subject, comprising analyzing a biological sample from a subject selected from of urine, blood, sputum, brochoalveolar lavage (BAL) cells and peripheral blood mononuclear cells (PBMCs); determining if the subject has elevated p-MSK1 levels as compared to a control level; and administering a therapeutically effective amount of an MSK1 inhibitor to the subject if an elevated p-MSK1 level is present.

In various aspects of the invention, the biological sample from the subject can be urine, blood, sputum, bronchoalveolar lavage (BAL) cells or peripheral blood mononuclear cells (PBMCs).

In other aspects of the invention, the inflammatory disease is selected from an inflammatory bowel disease, allergic rhinitis, sinusitis, atopic dermatitis, psoriasis, arthritis, an inflammatory lung disease, interstitial lung disease, sarcoidosis, and an autoimmune inflammatory disease. In still further aspects, the inflammatory lung disease can be associated with a chronic obstructive disease (COPD) of the airways. In yet other aspects, the inflammatory lung disease can be associated with viral induced inflammation. In still other aspects, the inflammatory lung disease is triggered by the subject's exposure to environmental conditions. The environmental conditions can include second hand smoke, primary tobacco smoke, or an allergen. The allergen can include pollen or animal allergens. In still further aspects, the inflammatory lung disease is asthma. In yet another aspect, the subject is being administered a non-steroid anti-inflammatory drug.

In still another aspect of the invention, the subject is a human.

BRIEF DESCRIPTION OF THE DRAWINGS

FIGS. 1A-1G show the composition of the airway microbiome based on 16s RNA sequencing of the bacterial DNA isolated from BAL samples from normal controls (i.e. healthy individuals with no known allergies) and asthma patients. Significant alterations in the compositions of airway microbiome in asthmatics as compared to normal controls are shown in FIG. 1A and FIG. 1C. A mean % of major bacterial phyla per group is presented. No differences in bacterial load in the study groups tested based on 16s RNA copy number are shown in FIGS. 1B and 1D. Alterations in the % major commensal organisms genera *Prevotella* (FIG. 1E), *Veillonella* (FIG. 1F) and bacterial diversity (FIG. 1G) in the airway microbiome of asthma patients with and without bacterial expansions as compared to normal controls are demonstrated. *$p<0.05$, **$p<0.01$ as compared to normal control.

FIGS. 4A-4D show the influence of TLR pathway inhibitors on cellular response to corticosteroids in the presence of bacteria. Pretreatment of asthmatic peripheral blood monocytes with TAK1 but not p38 MAPK or p38 MAPK/ERK/JNK inhibitors results in significant inhibition of MKP-1 mRNA (FIG. 4A) and IL-8 mRNA (FIG. 4B) induction by *H. parainfluenzae* (H para) and restoration of cellular sensitivity to corticosteroids in vitro (FIG. 4C) as shown by real time PCR. (FIG. 4D) 2 μM TAK1 and 10 μM p38 inhibitors fully inhibited activation of downstream signaling targets in response H para. Phosphorylation of ERK and hsp27 as a downstream read out targets for TAK1 and p38 MAPK activation, respectively, in response to 15 min of treatment of monocytes from asthma patients with H para (bacteria to cell ratio 1:1) with and without corresponding inhibitor is shown by Western blot. For IL-8 mRNA and MKP-1 mRNA production the cells were cultured overnight in X-VIVO™ 15 medium, incubated with inhibitors for 1h, stimulated with bacteria for 15 min followed by 3h of treatment with $10^{-6}$M DEX or medium and analyzed by real time PCR. Bacteria were added to $0.5 \times 10^6$ cells per condition (bacteria to cell ratio 1:1). The responses of monocytes from 4 asthmatics were examined.

FIGS. 5A-5B show the increased IL-8 mRNA and LPS levels in BAL samples from CR asthmatics with distinct gram-negative bacteria expansions in the airways. CR asthmatics with expansions of unique gram-negative bacteria in the airways have significantly elevated levels of IL-8 mRNA expression by BAL cells (FIG. 5A) and increased levels of LPS in BAL fluid (FIG. 5B) as compared to CR asthmatics with expansions of gram-negative bacteria that are common between CR and CS asthmatics.

DETAILED DESCRIPTION OF THE INVENTION

Figure 1A:
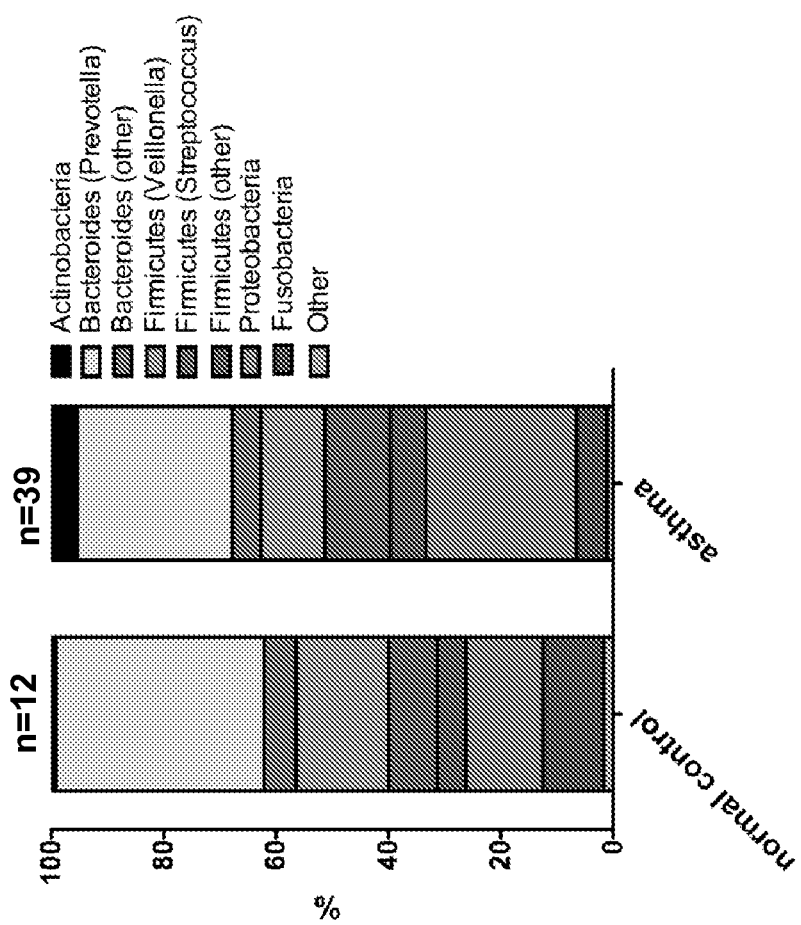

The inventors have demonstrated for the first time, that expanded pathogenic microbial communities residing in the airways of a subset of CR asthmatics can serve as triggers for airway cell activation and inhibit cellular responses to corticosteroids. In addition, the inventors previously demonstrated that there were significant levels of endotoxin in the BAL fluid of SR asthmatics (Goleva E et al., *J Allergy Clin Immunol* 2008; 122:550-559 e553), and that along with high endotoxin levels in BAL fluid, BAL macrophages of these subjects demonstrated classical macrophage activation and induction of LPS signaling pathways (Goleva E et al., *J Allergy Clin Immunol* 2008; 122:550-559 e553). The inventors have now determined MAPK activation in BAL and peripheral blood of steroid resistant (SR) and steroid sensitive (SS) asthmatics as well as MAPK activation in peripheral blood mononuclear cells (PBMC) of SR asthmatics.

This invention generally relates to methods of identifying and treating subjects having an inflammatory disease resistant to corticosteroid treatment. The methods include detecting the expansion and/or presence of one or more gram-negative bacteria in a subject; detecting the expression of transforming growth factor beta associated kinase-1 (TAK1) in a subject; determining the level of phosphorylated TAK1 (p-TAK1) in a subject; as well as by determining the level of phosphorylated MSK1 (p-MSK1) in a subject. The invention further relates to methods of predicting the response of subject to corticosteroid treatment as well as to the use of TAK1 inhibitors, p-TAK1 inhibitors, MSK1 inhibitors and p-MSK1 inhibitors in treating inflammatory diseases resistant to corticosteroid treatment.

As demonstrated in Examples 1-5 below, the inventors demonstrate for the first time that expanded pathogenic microbial communities residing in the airways of a subset of CR asthmatics can serve as triggers for airway cell activation and inhibit cellular responses to corticosteroids.

In one aspect of the invention, the subject can be identified as having an inflammatory disease resistant to corticosteroid treatment by detecting the expansion and/or presence of one or more gram-negative bacteria in a biological sample from the subject as compared to a control. The gram-negative bacteria can be any gram negative bacteria with a Lipid A chain length of 14 carbons or less, including but not limited to *Tropheryma, Leptotrichia, Neisseria, Simonsiella, Haemophilus*, and *Campylobacter*. The subject can be identified as having an inflammatory disease resistant to corticosteroid treatment, if the subject has unique gram-negative bacteria that are not found in the airways of the control. Additionally, if the expansion of the gram-negative bacteria is determined to be at least 2-fold greater than the gram-negative bacteria found in the airways of the control, then the subject can be identified as having an inflammatory disease resistant to corticosteroid treatment.

In another aspect of the invention, the response of a subject, who has, or is at risk of developing an inflammatory disease resistant to corticosteroid treatment can be predicted by obtaining a biological sample from the subject; and analyzing in the biological sample for the expansion of at least one gram-negative bacteria; wherein the expansion of the of at least one gram-negative bacteria compared to a control predicts the subject to be resistant to corticosteroid treatment. In still another aspect, the response can be predicted by determining the presence of at least one gram-negative bacteria that is not normally found in the normal controls.

The expansion of one or more gram-negative bacteria in a biological sample from the subject as compared to a control can identify the subject as having an inflammatory disease resistant to corticosteroid treatment. In addition, the presence of one or more gram-negative a biological sample from the subject as compared to a control can also identify the subject as having an inflammatory disease resistant to corticosteroid treatment. The expansion as well as the presence of the gram-negative bacteria can be determined by methods known to those of skill in the art and include 16S rRNA sequencing of bacterial DNA extracted from the biological samples, PCR or real-time PCR with primers to identify specific bacterium and/or microbiological culture techniques known in the art. The biological sample can be from serum, plasma, blood, urine, sputum, peripheral blood mononuclear cells (PBMCs), epithelial cells, sinus tissue, nasal tissue, skin biopsy and bowel biopsy of both the subject as well as the control.

In one aspect of the invention, the control can be a healthy individual who has been previously determined to not have an inflammatory disease resistant to corticosteroid. As referred to herein a "normal control", is a subject (or a group of subjects) that has no known allergies. In another aspect, the control is a steroid sensitive (SS) subject (or group of SS subjects). In one aspect of the invention, the subject's level is compared to a control level that has been determined from multiple control subjects (normal control subjects and/or SS subjects) that are similar in age, gender, and race as the subject. Thus, a normal control or SS control can be a control from a group of control subjects. In still another aspect, the subject's biological sample and the control biological sample can be from the same or different biological location. In a preferred aspect, the biological sample is from the same biological location.

As used herein, steroid sensitive (SS) indicates that a subject responds to steroids with improved lung function and/or any other disease activity marker that is being monitored. Steroid resistant (SR) indicates that a subject has no response to steroids thus no improvement in lung function and/or any other disease activity marker that is being monitored.

In still another aspect, the subject can be identified as having an inflammatory disease resistant to corticosteroid treatment by detecting the expression of transforming growth factor beta associated kinase-1 (TAK1) in a biological sample from the subject. In one aspect, an increased expression of TAK1 compared to a sample from a control identifies the subject as having an inflammatory disease resistant to corticosteroid treatment. The expression of TAK1 from the subject is compared to the expression of TAK1 from a control. The control can be steroid sensitive or a normal control.

In yet another aspect, the subject can be identified as having an inflammatory disease resistant to corticosteroid treatment by determining the level of phosphorylated TAK1 (p-TAK1) in a biological sample from the subject, wherein an elevated level of p-TAK1 compared to a control identifies the subject as having an inflammatory disease resistant to corticosteroid treatment. The level of p-TAK1 from the subject is compared to the level of p-TAK1 from a control. The control is steroid sensitive or a normal control. An elevated level of p-TKA1 is determined to be at least two fold greater that the control.

In another aspect of the invention, the response of a subject, who has, or is at risk of developing an inflammatory disease resistant to corticosteroid treatment can be predicted by obtaining a biological sample from the subject; and analyzing in the biological sample for the activity of TAK1; wherein an increase or decrease in TAK1 activity compared to a control predicts the subject to be resistant to corticosteroid treatment. An increase in TAK1 activity is determined to be at least 2 fold greater than the TAK1 activity in the control as determined by methods including but not limited to real time PCR, Western blot, and a kinase activity assay as compared to the control. A decrease in TAK1 activity is determined to be at least 2 fold lower than the TAK1 activity in the control as determined by methods including but not limited to real time PCR, Western blot, and a kinase activity assay as compared to the control. In a preferred aspect, the control is steroid sensitive or a normal control.

The inflammatory disease can be an inflammatory lung disease, an inflammatory bowel disease, allergic rhinitis, sinusitis as well gram negative sepsis. The inflammatory lung disease can be associated with a chronic obstructive disease of the airways as well as associated with viral induced inflammation. The inflammatory lung disease can be triggered by the subject's exposure to environmental conditions, including but not limited to second hand smoke, primary tobacco smoke, and an allergen. Allergens can include pollen or animal allergens. In a preferred aspect, the inflammatory lung disease is asthma.

In yet another aspect of the invention, the subject is being administered a non-steriodal anti-inflammatory drug.

One embodiment of the invention relates to the a method of treating a subject having an inflammatory disease resistant to corticosteroid treatment by administering to the subject a compound that inhibits transforming growth factor beta associated kinase-1 (TAK1) activity. Another embodiment of the invention relates to a method for diagnosing and treating an inflammatory disease resistant to corticosteroid treatment in a subject comprising analyzing a subject sample for the presence of p-TAK1, wherein the subject is diagnosed as having an inflammatory disease resistant to corticosteroid treatment if the p-TAK1 level is elevated compared to a control p-TAK1 level, and administering a compound that inhibits TAK1 activity to the diagnosed subject.

The control p-TAK1 level can be determined from a steroid sensitive control or a normal control. An elevated level of p-TAK1 is determined to be at least two fold greater than the control p-TAK1 level.

The compound that can inhibit TAK1 activity can be a compound that is a TAK1 inhibitor which can inhibit the activity of TAK1 and/or the expression of TAK1. The TAK1 inhibitor can include a small small-molecule inhibitor, a chemical inhibitor, and antibody as well as TAK1 siRNA. In one aspect, the compound can be a non-steroidal anti-inflammatory drug. The inhibitor can also be a compound that can inhibits the phosphorylation of TAK1.

As indicated above, the inflammatory disease can be an inflammatory lung disease, an inflammatory bowel disease, allergic rhinitis, sinusitis as well gram negative sepsis. The inflammatory lung disease can be associated with a chronic obstructive disease of the airways as well as associated with viral induced inflammation. The inflammatory lung disease can be triggered by the subject's exposure to environmental conditions, including but not limited to second hand smoke, primary tobacco smoke, and an allergen. In a preferred aspect, the inflammatory lung disease is asthma.

In still another aspect, A TAK1 inhibitor for use in the treatment of an inflammatory disease resistant to corticosteroid treatment in a subject with p-TAK1 levels that are elevated as compared to a control p-TAK1 level. An elevated p-TAK1 is determined to be at least 2 fold greater than the control p-TAK1 level. Yet another aspect of the invention is a TAK1 inhibitor for use in treating an inflammatory disease resistant to corticosteroid treatment in a patient, comprising analyzing a biological sample from a subject selected from the group consisting of serum, plasma, blood, urine, sputum, peripheral blood mononuclear cells (PBMCs), epithelial cells, sinus tissue, nasal tissue, skin biopsy and bowel biopsy; determining if the subject has elevated p-TAK1 levels as compared to a control; and administering a therapeutically effective amount of an TAK1 inhibitor to the subject if an elevated p-TAK1 level is present.

As demonstrated in Examples 1-5, bacterial 16s rRNA gene sequencing was performed on bronchoalveolar lavage (BAL) samples of 29 corticosteroid resistant (CR), 10 corticosteroid sensitive (CS) asthmatics and 12 healthy controls (i.e. normal controls). Asthmatic BAL macrophages were stimulated with pathogenic versus commensal microorganisms, and analyzed for the expression of corticosteroid-regulated genes IL-8 and mitogen activated kinase phosphatase (MKP-1) by real-time PCR. Cellular p38 mitogen activated protein kinase (MAPK) activation was assessed by Western blot.

Overall 33 out of 39 asthmatics had expansions of specific groups of microorganisms (gram-negative bacteria) (>5% of 16s rRNA sequences, >2 fold increase above microbes present in normal (control) airways or unique organisms not found in normal airways) and significant reduction of airway commensals, genera Prevotella and Veillonella ($p<0.01$). Fourteen CR asthmatics had unique microbial expansions in the airways; these were mainly gram-negative bacteria. Preincubation of asthmatic airway macrophages with Haemophillus parainfluenzae, a distinct pathogenic organism in CR asthma airways, but not Prevotella melaninogenica, resulted in p38 MAPK activation, increased IL-8 ($p<0.01$) and MKP-1 mRNA ($p<0.01$) production and inhibition of cellular responses to corticosteroids ($p<0.05$). Inhibition of transforming growth factor beta associated kinase-1 (TAK1), upstream activator of MAPK, but not p38 MAPK restored cellular sensitivity to corticosteroids.

A subset of CR asthmatics demonstrated airway expansion of unique gram-negative bacteria, which trigger TAK1/ MAPK activation and induce corticosetroid resistance. An inhibitor of TAK1 activation restored cellular sensitivity to corticosteroids induced by these bacteria.

As further demonstrated in Example 1-5, BAL microbiome in 39 asthma patients and 12 normal control subjects were evaluated. Significant alterations in the airway microbiome composition were noted in asthmatics as compared to normal controls. There were no observed differences in bacterial load between samples from asthmatics and normal controls, suggesting that these microbial expansions in asthmatics were not a result of infection, but rather changes in the qualitative composition of the bacterial communities that reside in the airways of asthmatics. In contrast to previous reports (Hilty M, et al. *PLoS One* 2010; 5:e8578; Huang Y J, et al. *J Allergy Gin Immunol* 2011; 127:372-81 e1-3), the inventors found no significant differences in the microbiome diversity between normal controls and asthma group as a whole were observed. However, 33 (24 CR and 9 CS asthmatics) out of 39 asthmatics had expansions of specific groups of microorganisms (>5% of 16s rRNA sequences, >2 fold increase above microbes present in normal controls or distinct organisms). A reduction of the airway commensals, genera Prevotella and Veillonella, reduction in phylum Fusobacteria and expansions of phyla Actinobacteria and Proteobacteria were observed in asthmatics with bacterial expansions. Asthmatics with no bacterial expansions were also abnormal with significant increases in number of sequences for Prevotella and Veilonella but depletions of other bacterial phyla and less diversified microbial communities.

The asthmatics in Examples 1-5, were defined clinically as responsive or non-responsive to corticosteroid treatment based on an oral prednisone burst (CR and CS asthmatics). The inventors examined whether there were specific alterations in the airway microbiome composition in CR asthmatics. The inventors found that a subset of CR asthmatics (14 patients out of 29) had distinct microbial expansions in the airways. Microorganisms, found to be uniquely expanded in the airways of CR asthmatics were mainly gram-negative LPS producing bacteria (Table 1). Importantly, these patients had significantly higher IL-8 expression by BAL cells and significantly elevated levels of LPS in the BAL fluid, suggesting microbial stimulation. These data are in agreement with a previous report of classical macrophage activation and induction of LPS signaling pathways in BAL cells from subjects with CR asthma (Goleva E et al., *J Allergy Clin Immunol* 2008; 122:550-9).

TABLE 1

Microorganisms expanded in the airways asthma patients*

| Types of organisms | | CR asthma, n = 29, patients with bacterial expansions, (n)** | CS asthma, n = 10, patients with bacterial expansions, (n) | Microorganisms present in the airways of normal controls, Y/N (average % out of total 16s rRNA sequences) |
|---|---|---|---|---|
| Actinobacteria: | | 7 | 2 | |
| | Propionibacterium | 3 | 1 | Y (0.1%) |
| | Rhodococcus | 4 | 1 | N |
| | *Tropheryma* | 1 | 0 | N |
| Bacteroides: | | 5 | 2 | |
| | Porphyromonas | 5 | 2 | Y (4.4%) |
| Cyanobacteria: | | 0 | 1 | |
| | Streptophyta | 0 | 1 | Y (0.4%) |

TABLE 1-continued

Microorganisms expanded in the airways asthma patients*

| Types of organisms | | CR asthma, n = 29, patients with bacterial expansions, (n)** | CS asthma, n = 10, patients with bacterial expansions, (n) | Microorganisms present in the airways of normal controls, Y/N (average % out of total 16s rRNA sequences) |
|---|---|---|---|---|
| Firmicutes: | | 8 | 5 | |
| | Geobacillus | 2 | 1 | Y (0.5%) |
| | Leuconostoc | 1 | 0 | N |
| | Megasphaera | 1 | 0 | Y (1.2%) |
| | Streptococcus | 6 | 4 | Y (8.6%) |
| Fusobacteria: | | 4 | 1 | |
| | Fusobacterium | 0 | 1 | Y (6.3%) |
| | Leptotrichia | 4 | 0 | Y (4.2%) |
| Proteobacteria: | | 17 | 6 | |
| α-proteobacteria | Asticcacaulis | 5 | 2 | N |
| | Bradyrhizobium | 0 | 1 | N |
| β-proteobacteria | Acidovorax | 5 | 2 | N |
| | Aquabacterium | 0 | 1 | N |
| | Comamonas | 4 | 2 | N |
| | Limnobacter | 0 | 1 | N |
| | Methylophilus | 2 | 1 | N |
| | Neisseria | 5 | 0 | Y (6.0%) |
| | Simonsiella | 1 | 0 | Y (0.5%) |
| γ-proteobacteria | Haemophilus | 2 | 0 | Y (2.9%) |
| | Pasteurella | 0 | 1 | Y (0.6%) |
| ε-proteobacteria | Campylobacter | 1 | 0 | Y (3.2%) |

*Microorganisms were considered as expanded in asthma airway microbiome if they represented over 5% out of total 16s rRNA sequences and the % of sequences was increased at least 2 fold over controls for the organisms present both in the airways of asthmatics and normal control; for the Genera found only in asthma patients microorganisms were considered as expanded if they represented over 5% of the total 16s RNA sequences.
**Microorganisms uniquely expanded in CR asthma airways are shown in bold font.

To date, functional interaction of the microbiome with airway cells, including BAL macrophages, and its effects on cellular response to corticosteroids have not been investigated. The inventors chose one of the microorganisms from Proteobacteria phylum, expanded in the airways of CR asthmatics (*H. parainfluenzae*), and a commensal microorganism found in the airways (*P. melaninogenica*) to examine functional responses of cells from asthmatics to these bacteria in the presence of DEX. High levels of p38 MAPK activation and reduced cellular responses to corticosteroids occurred in the presence of *H. parainfluenzae*, but not commensal, bacteria, in both peripheral blood monocytes and BAL macrophages from asthmatics, Examples 1-5 below demonstrate intrinsic differences in cell stimulating properties between commensal versus expanded pathogenic bacteria associated with CR asthma airway microbiota. These differences are believed to be due related to the differences in lipid A structures of bacterial LPS, which have different immunostimulatory properties. Bacterial LPS is composed of three distinct regions—lipid A, a short core oligosaccharide, and the O-antigen polysaccharide (Raetz C R, *Annu Rev Biochem* 2002; 71:635-700). Lipid A anchors the molecule in the outer membrane and is the bioactive component recognized by TLR4 (Raetz C R et al., *Annu Rev Biochem* 2007; 76:295-329). Lipid A structures of various microorganisms show wide heterogeneity (Raetz C R et al., *Annu Rev Biochem* 2007; 76:295-329) which influence its stimulatory potency (Netea M G et al., *Trends Immunol* 2002; 23:135-9; Miller S I et al., *Nat Rev Microbiol* 2005; 3:36-46; Erridge C et al., *Microbes Infect* 2002; 4:837-51) and interaction with TLR4 (Park B S et al., *Nature* 2009; 458:1191-5). Lipid A structures with the shorter length and number of acyl chains are more immunostimulatory. As disclosed herein, *H. parainfluenzae* lipid A has C14 acyl chains, similar to *E. coli* LPS, while *P. melaninogenica* lipid A has longer C16-C18 acyl chains (Erridge C et al., *Microbes Infect* 2002; 4:837-51). *Prevotella* LPS structure and its weak stimulatory activity for TLR4 has already been shown (Hashimoto M et al., *FEBS Lett* 2003; 543:98-102). The difference in LPS composition between LPS-producing commensal and pathogenic microorganisms in the airways (Netea M G et al., *Trends Immunol* 2002; 23:135-9; Miller S I et al., *Nat Rev Microbiol* 2005; 3:36-46; Erridge C et al., *Microbes Infect* 2002; 4:837-51; Larsen J M et al., *PLoS One* 2012; 7:e31976) is believed to account for airway cell activation only by pathogenic bacteria and results in altered cellular response to corticosteroids.

Persistent infection and colonization with pathogenic bacteria may be difficult to eradicate with antibiotic treatment (Kong H H et al., *Genome Res* 2012; 22:850-9) therefore alternative approaches are needed. The inventors determined whether inhibition of TAK1 and MAPK activation by bacteria via TLR by selective inhibitors would restore cellular responses to corticosteroids in the presence of pathogenic bacteria. The inventors found that TAK1 inhibitor-treated cells were steroid sensitive despite incubation with *H. parainfluenzae*. MAPK inhibitors reduced IL-8 and MKP-1 mRNA induction by *H. parainfluenzae* but did not restore cellular sensitivity to corticosteroids in the presence of *H. parainfluenzae*. The data support that activation of TAK1 by bacteria is essential in alteration of cellular responses to corticosteroids.

The data disclosed in Examples 1-5 demonstrate distinct expansion of gram-negative microorganisms in the airways of a subset of CR asthmatics, thus providing a biomarker for personalized asthma approaches to management. These microorganisms can trigger airway cell activation, making these cells less responsive to corticosteroids in vitro. The data also demonstrate that TAK1 inhibitor reverses cellular resistance to corticosteroids in the presence of pathogenic bacteria. Based on the data presented herein that airway cell stimulation by bacteria as a result of alterations in the airway microbiome composition and microbial expansions can inhibit cellular response to corticosteroids and influence efficacy of corticosteroid treatment.

Subjects evaluated in the study described in Examples 1-5 remained symptomatic as reflected by the ACQ score. It is possible that lack of response to steroids in the host allows such microbial expansions as persistent inflammation may impair host defense. The inventors did not observe selective expansions of microorganisms in subjects that were treated with ICS at the time of evaluation as opposed to subjects that were not on ICS.

Recent literature suggests that commensal microbiota maintains and shapes normal mucosal immunity in the gut (Summary and recommendations of a workshop on the investigative use of fiberoptic bronchoscopy and bronchoalveolar lavage in asthmatics. *Am Rev Respir Dis* 1985; 132:180-2; Guidelines for fiberoptic bronchoscopy in adults. American Thoracic Society. Medical Section of the American Lung Association. *Am Rev Respir Dis* 1987; 136:1066). Similarly, it has been reported that *Staphylococcus epidermidis*, a commensal organism in the skin, can protect the host from development of injurious inflammation by tolerizing the response via TLR (Busse W W et al., *Am J Respir Crit Care Med* 2005; 172:807-16). By analogy, it is possible that commensal microbiota in the airways is protective from development of inflammatory responses; and loss of commensal organisms allows cellular inflammatory response. Restoration of the commensal microbiota in the airways of asthmatics may be evaluated for its protective role and alleviation of cellular steroid response in the airways of asthmatics, such as those patients with chronic rhinosinusitis. It has been shown recently that sinus microbiota of patients with chronic rhinosinusitis exhibits significantly reduced bacterial diversity compared with that of healthy controls (Goleva E et al., *J Allergy Clin Immunol* 2008; 122:550-9). Multiple, phylogenetically distinct lactic acid bacteria were depleted concomitant with an increase in the relative abundance of a single species, *Corynebacterium tuberculostearicum* (Goleva E et al., *J Allergy Clin Immunol* 2008; 122:550-9). In a murine model of rhinosinusitis *Lactobacillus sakei*, a commensal organism from the sinuses, defended against *C. tuberculostearicum* sinus infection, even in the context of a depleted sinus bacterial community (Goleva E et al., *J Allergy Clin Immunol* 2008; 122:550-9).

It was shown recently that the composition of BAL bacterial communities in healthy controls is similar but lower in burden then those from upper airways of these subjects (Magurran A E. Measuring Biological Diversity: Wiley; 2003). Whether such findings reflect contamination during lower airway sampling by upper airway microbiota, or low-level colonization via inhalation or microaspiration of organisms into the lower airways requires further studies. As disclosed in Examples 1-5, comparison of bacterial 16s rRNA gene sequences between five matching BAL samples and oropharyngeal swabs demonstrated only marginal overlap (Mean±SD, 62±36% similarity based on the Morisita-Horn beta diversity analysis). Some of the microorganisms that were found expanded in the airways of asthmatics are not typical representative of the upper airway microbiota. But it is possible that they were acquired from patients' environment, and then "trapped" in the lower airways due to failed clearance.

Mitogen and stress activated protein kinase 1 (MSK) is known to be activated by p38 MAPK in response to growth factors and cellular stress (Deak M et al., *EMBO J* 1998; 17:4426-4441), and thus the inventors assessed MSK1 activation as evidence for p38 MAPK pathway activation. Recent advances in phospho-flow cytometry have made it possible to simultaneously measure intracellular proteins and surface markers of various cell populations. Therefore the inventors determined that MAPK activation is also observed in peripheral blood mononuclear cells (PBMC) of SR asthmatics.

One embodiment of the invention relates to a method to identify a subject having an inflammatory disease resistant to CS treatment by determining the level of phosphorylated MSK1 (p-MSK1) in a biological sample from the subject. In one aspect, the step of determining the subject's p-MSK1 level includes determining the subject's p-MSK1 level, wherein an elevated level in the subject as compared to a control p-MSK1 level identifies the subject as having an inflammatory disease resistant to corticosteroid treatment. In one aspect, the control is a steroid sensitive control or a normal control. In another aspect, the subjects MSK1 mRNA expression level may be determined, wherein an elevated MSK1 mRNA expression level as compared to a control MSK1 mRNA expression level identifies the subject as having an inflammatory disease resistant to corticosteroid treatment. In one aspect, the elevated level is determined to be at least 2 fold greater than the control.

Another embodiment of the invention relates to a method for diagnosing and treating an inflammatory disease resistant to corticosteroid treatment in a subject comprising analyzing a subject sample for the presence of p-MSK1, wherein the subject is diagnosed as having an inflammatory disease resistant to corticosteroid treatment if the p-MSK1 level is elevated compared to a control p-MSK1 level, and administering a compound that inhibits MSK1 activity to the diagnosed subject. The control can be a steroid sensitive control or a normal control.

Another embodiment of the invention relates to a method of treating a subject having an inflammatory disease resistant to CS treatment by administering to the subject a compound that inhibits MSK1 activity. In one aspect, the compound can be an MSK1 inhibitor. The MSK1 inhibitor can be a small molecule inhibitor, a chemical inhibitor, an antibody or a MSK1 siRNA. The MSK1 inhibitor can inhibit the activity and/or expression of MSK1 and/or can inhibit the phosphorylation of MSK1.

Another embodiment of the invention relates to a method to predict the response of a subject to CS treatment, who has, or is at risk of developing an inflammatory disease resistant to CS treatment, comprising obtaining a biological sample from the subject, analyzing in the biological sample for at least one marker wherein the marker can be an elevated level of p-MSK1 or an elevated levels of phosphorylated p-38 and wherein an elevated level of at least one marker compared to a control predicts the subject to be resistant to corticosteroid treatment. In one aspect, the marker is an elevated level of p-MSK1. In another aspect, the control level may be a p-MSK1 level determined from a steroid sensitive control or a normal control. In yet another aspect, the control level may be a phosphorylated p38 level determined from a steroid sensitive control or a normal control. An elevated level is determined to be a level at is at least two fold greater than the control.

Another embodiment of the invention relates to a method to identify a subject as having an inflammatory disease sensitive to CS treatment by determining the level of phosphorylated MSK1 (p-MSK1) in a biological sample from the subject. In one aspect, the step of determining the subject's p-MSK1 level includes determining the subject's p-MSK1 level, wherein a low level in the subject as compared to a control p-MSK1 level identifies the subject as having an inflammatory disease sensitive to corticosteroid treatment. A low level is determined to be at least two fold lower than a steroid sensitive control or a normal control.

In another aspect, the step of determining the subject's p-MSK1 level includes determining the subject's p-MSK1 level, wherein an elevated level in the subject as compared to a control p-MSK1 level identifies the subject as having an inflammatory disease sensitive to corticosteroid treatment. In one aspect, the level is elevated over the control level but is less than a 1.5 fold increase.

Another embodiment of the invention relates to a MSK1 inhibitor for use in the treatment of an inflammatory disease resistant to corticosteroid treatment in a subject with p-MKS1 levels that are elevated as compared to a control p-MSK1 level. An elevated level is determined to be a level at is at least two fold greater than the p-MSK1 control level.

Another embodiment of the invention relates to a MSK1 inhibitor for use in treating an inflammatory disease resistant to corticosteroid treatment in a subject, comprising analyzing a biological sample from a subject selected from the group consisting of urine, blood, sputum, brochoalveolar lavage (BAL) cells and peripheral blood mononuclear cells (PBMCs); determining if the subject has elevated p-MSK1 levels as compared to a control level; and administering a therapeutically effective amount of an MSK1 inhibitor to the subject if an elevated p-MSK1 level is present.

The biological sample from the subject can be urine, blood, sputum, bronchoalveolar lavage (BAL) cells or peripheral blood mononuclear cells (PBMCs).

When determining the level of MKS1 or p-MSK1, the inflammatory disease can be an inflammatory bowel disease, allergic rhinitis, sinusitis, atopic dermatitis, psoriasis, arthritis, an inflammatory lung disease, interstitial lung disease, sarcoidosis, and an autoimmune inflammatory disease. In still further aspects, the inflammatory lung disease can be associated with a chronic obstructive disease (COPD) of the airways as well as be associated with viral induced inflammation. The inflammatory lung disease can be triggered by the subject's exposure to environmental conditions, including but not limited to second hand smoke, primary tobacco smoke, or an allergen. The allergen can include pollen or animal allergens. In still further aspects, the inflammatory lung disease is asthma. In yet another aspect, the subject is being administered a non-steroid anti-inflammatory drug.

In still another aspect of the invention, the subject and/or patient is a human.

Other aspects, kits are considered. In some aspects, the kits can include an antibody, detection ability as well as quantification ability. The detection ability can be immunofluoresence. In one aspect, the kit can include an inhibitor for TAK1, p-TAK1, MSK1, p-MSK1 or combinations thereof.

As further demonstrated in Examples 6-9 below there is a selective increase in p38 activation of BAL macrophages and PBMC of SR compared with SS asthmatics. Phosphoflow cytometric analysis demonstrated that the increase of p38 phosphorylation occurred in circulating $CD14^+$ cells from SR asthmatics. This differential p38 activation was not observed in $CD4^+$, $CD8^+$ T cells, B cells and NK cells. The inventors provide evidence for p38 pathway activation in SR asthmatics as shown by significant increase in MSK1 phosphorylation and IL-6 mRNA production by the cells of SR asthmatics.

The inventors previously showed that the expression of multiple inflammatory genes related to classical macrophage activation in BAL cells from SR asthmatics as compared with SS asthmatics (Goleva E et al., *J Allergy Clin Immunol* 2008; 122:550-559 e553). Since MAPK activation is one of the key downstream pathways involved in the macrophage activation, the inventors studied the expression of activated kinase members of the mitogen-activated protein kinase family (p38, ERK, JNK) in BAL macrophages by immunofluorescence staining. Activated ERK, JNK and p38 MAPK had been found in pulmonary macrophages, airway epithelial cells, alveolar macrophages of patients with asthma (Chung K F, *Chest* 2011; 139:1470-1479; Liu W et al., *Mol Cell Biol* 2010; 30:1783-1799; Shan L et al., *J Immunol* 2010; 184:7134-7143) and several studies have demonstrated association between the clinical severity of asthma and expression of p-ERK and p-p38 in asthmatic airways (Liu W et al., *J Allergy Clin Immunol* 2008; 121:893-902 e892). p38 MAPK was also demonstrated to regulate the production of many pro-inflammatory cytokines such as IL-8, IL-6, TNF-α; increased levels of IL-8 and TNF-α have been found in BAL macrophages from SR asthmatics (Liu W et al., *J Allergy Clin Immunol* 2008; 121:893-902 e892). In a recent study, Bhaysar et al. stimulated alveolar macrophages from asthma patients of different severities with LPS and concluded that steroid responsiveness was correlated with the degree of p38 MAPK activation (Bhaysar P et al., *Eur Respir J* 2010; 35:750-756). Unlike the Bhaysar study that used in vitro LPS stimulation, the inventors compared the basal expression of p-MAPKs in BAL macrophages between SR asthmatics and SS asthmatics. The results showed both p-p38 and p-ERK activation was increased in BAL macrophages from SR asthma group. Interestingly, further experiments found that PBMC demonstrated enhanced p38 phosphorylation as well in circulating $CD14^+$ cells of SR asthmatics. To the best of the inventors' knowledge, this is the first report of enhanced p38 phosphorylation in BAL macrophages and circulating blood $CD14^+$ from patients with SR asthma compared with SS asthma.

P38 consists of four subtypes (p38alpha-delta), which regulate cellular activities by serving as phosphorylation substrates of its upstream kinases, and also phosphorylates specific serines and threonines of its downstream substrates. Downstream of p38, there is MSK1, which can mediate phosphorylation of histone H3 on serine at different inflammatory gene promoters to stimulate their transcription (Vermeulen L et al., *EMBO J* 2003; 22:1313-1324). However, GCs counteract the recruitment of activated MSK1 at inflammatory gene promoters resulting in the inhibition of NF-43, p65 transaction and concurrent histone H3 phosphorylation (Beck I M et al., *Biochem Pharmacol* 2009; 77:1194-1205). In another example of interaction between the GCR and MSK1, MSK1 predominantly localizes in the nucleus however activated GCR can translocate p-MSK1 from the nucleus to the cytoplasm (Beck I M et al., *EMBO J* 2008; 27:1682-1693). As shown herein, the inventors detected an increase in activated MSK1 that paralleled the increase of phosphorylated p38 in PBMC from SR asthma, indicating the involvement of MSK1 in regulation of cellular steroid responses.

The results presented in Examples 6-9 on p38 and MSK1 activation in peripheral blood monocytes of SR asthma demonstrates that events in the airway can be reflected in the activation of peripheral blood cells. Peripheral blood from subjects can be readily analyzed, thus, p-p38 and p-MSK1 can be used to evaluate PBMC as predictors of asthmatic responsiveness to corticosteroid treatment.

The following examples are provided for illustrative purposes, and are not intended to limit the scope of the invention as claimed herein. Any variations which occur to the skilled artisan are intended to fall within the scope of the present invention. All references cited in the present application are incorporated by reference herein to the extent that there is no inconsistency with the present disclosure.

EXAMPLES

Materials and Methods for Examples 1-5

Study Subjects.

Thirty-nine adult asthmatics were enrolled in this study. All patients had baseline $FEV_1$ percent predicted 85% and demonstrated significant airway hyperresponsiveness (PC20 methacholine, <10 mg/mL) and/or significant bronchodilator responsiveness (>12% improvement in $FEV_1$ percent predicted after inhalation of 180 μg albuterol), as described (Goleva E et al., *J Allergy Clin Immunol* 2007; 120:1065-72; Goleva E et al., *Am J Respir Crit Care Med* 2006; 173:607-16; Sher E R et al., *J Clin Invest* 1994; 93:33-9; Hamid Q A et al., *Am J Respir Crit Care Med* 1999; 159:1600-4). Patients completed asthma questionnaires (ACQ) to assess their asthma control. After baseline characterization, all subjects underwent bronchoscopy, received prednisone, 20 mg by mouth twice daily, for 7 days and were categorized as corticosteroid sensitive (CS) asthmatics if the $FEV_1$ percent predicted value improved ≥15% and as CR asthmatics if the $FEV_1$ percent predicted value improved <10%. Twelve healthy nonatopic subjects underwent bronchoscopy as controls. Smokers were excluded from participation in this study. Informed consent was obtained from all study participants before enrollment in this study. Details of patient characteristics are presented in Table 2.

TABLE 2

| Patient characteristics | | | |
|---|---|---|---|
| | Normal controls n = 12 | CR asthma n = 29 | CS asthma n = 10 |
| Age, yrs, (Mean ± SD) | 31.1 ± 9.2 | 34.2 ± 11.1 | 37.9 ± 10.8 |
| Gender (Male/Female) | 4/8 | 14/15 | 2/18 |
| Race (C/AA/Other) | 11/0/1 | 19/4/6 | 9/0/1 |
| BMI, kg/m², (Mean ± SD) | 24.1 ± 4.7 | 26.3 ± 6.4 | 32.2 ± 8.5 |
| IgE, U/ml, (Mean ± SD) | 75 ± 108 | 253 ± 289 | 177 ± 211 |
| Number of positive skin tests | 0.1 ± 0.3 | 6 ± 4 | 6 ± 4 |
| PC20, μg/ml (Mean ± SD) | >25 | 1.5 ± 2.2 | 0.5 ± 0.6 |
| ACQ score (Mean ± SD) | NA | 1.5 ± 0.8 | 1.9 ± 0.6 |
| eNO, ppm (Mean ± SD) | NA | 34.9 ± 24.8 | 47.3 ± 29.2 |
| Baseline $FEV_1$ % predicted, (Mean ± SD) | 98.7 ± 11.7 | 76.3 ± 10.3 | 61.9 ± 16.1 |
| $FEV_1$ % reversal with Albuterol, (Mean ± SD) | 5.1 ± 2.4 | 15.0 ± 9.4 | 37.2 ± 24.7 |
| $FEV_1$ % change after Prednisone burst, (Mean ± SD) | NA | −0.2 ± 5.9* | 31.0 ± 23.5 |
| Corticosteroid medications** | | | |
| ICS/LABA | | 5 | 4 |
| ICS | | 7 | 0 |
| None | NA | 17 | 6 |

*p < 0.0001 as compared to CS asthmatics.
**For the CR and CS asthmatics that received ICS/LABA or ICS the Mean ± SD of the ICS dose in budesonide equivalents was 837 ± 713 μg and 1450 ± 1034 μg, respectively.

Specimen Collection.

Fiberoptic bronchoscopies with bronchoalveolar lavage (BAL) collection were performed for all study participants according to the guidelines of the American Thoracic Society (Summary and recommendations of a workshop on the investigative use of fiberoptic bronchoscopy and bronchoalveolar lavage in asthmatics. *Am Rev Respir Dis* 1985; 132:180-2; Guidelines for fiberoptic bronchoscopy in adults. American Thoracic Society. Medical Section of the American Lung Association. *Am Rev Respir Dis* 1987; 136:1066; Busse W W et al., *Am J Respir Crit Care Med* 2005; 172:807-16). BAL cells were prepared as described (Goleva E et al., *Am J Respir Crit Care Med* 2006; 173:607-16). 250 μl of BAL cell suspensions (1×10⁶/ml) were preserved at −80° C. prior to DNA extraction. BAL samples differentials are described below and Table 3.

Presence of LPS in the BAL fluid samples was analyzed by chromogenic limulus amebocyte lysate test as previously described (Goleva E et al., *J Allergy Clin Immunol* 2008; 122:550-9).

TABLE 3

BAL cell differentials for the samples from asthma patients and normal controls

| Parameters assessed | Normal controls, n = 12 | CR asthma, n = 29 | CS asthma, n = 10 |
|---|---|---|---|
| BAL, % return (mean ± SD) | 58.4 ± 9.9 | 52.5 ± 13.8* | 34.3 ± 14.9** |
| Total white blood cells (×10$^6$ [mean ± SD]) | 9.3 ± 7.3 | 7.1 ± 3.1 | 5.3 ± 5.1 |
| Macrophages/monocytes (% [mean ± SD]) | 90.9 ± 6.7 | 88.9 ± 9.2 | 83.8 ± 16.6 |
| Polymorphonuclear cells (% [mean ± SD]) | 1.3 ± 1.0 | 0.9 ± 0.9 | 2.1 ± 2.3 |
| Lymphocytes (% [mean ± SD]) | 5.5 ± 3.8 | 8.0 ± 8.4 | 12.3 ± 15.6 |
| Eosinophils (% [mean ± SD]) | 0.1 ± 0.1 | 0.6 ± 0.8*** | 1.6 ± 1.9**** |

*$p < 0.05$ as compared to CS asthma patients.
**$p < 0.01$,
***$p < 0.05$,
****$p < 0.001$ as compared to normal control subjects.

BAL differential analysis. BAL differentials were obtained on cytospin preparations by using a DIFF-QUICK® (Scientific Products, McGraw Park, Ill.) stain, counting a minimum of 500 cells. Significantly higher levels of eosinophils were found in BAL samples from patients with asthma as compared to normal control subjects ($p<0.01$, Table 3). In contrast, no significant differences were noted in the number of macrophages, lymphocytes and neutrophils in BAL samples between groups (Table 3).

Bacterial DNA Extraction and Sequencing.

Bacterial DNA extractions were performed from frozen BAL cell suspensions using the Qiagen EZ1® Advanced System per manufacturer's instructions. The bacterial DNA load of each sample was estimated using a 16s RNA TAQMAN® quantitative PCR assay described by Nadkarni (Nadkarni M A et al., Microbiology 2002; 148:257-66). 16s RNA copy number was established using a standard curve assembled from 10-fold serial dilutions of plasmid DNA containing a cloned rRNA gene.

Bacterial DNA were amplified in triplicate with barcoded (27F-338R) PCR primers that include adaptors for the Roche 454 sequencing platform (Mourani P M et al., PLoS One 2011; 6:e25959; Hamady M et al., Nat Methods 2008; 5:235-7). A negative PCR control was performed for each barcode. Amplicons were pooled after normalization for DNA concentration (Harris J K et al., Appl Environ Microbiol 2010; 76:3863-8), and sequenced per manufacturer's protocols using the Roche Genome Sequencer FLX system.

Sequence Analysis.

Sequence data was assigned to sample of origin using the bar code sequence added during PCR and screened for basic quality defects (short sequences <200 nucleotides in length, >1 sequence ambiguity, best read with quality over a 10 nucleotide moving window) by the software program BAR-TAB (Frank DN, BMC Bioinformatics 2009; 10:362). Non-bacterial sequences were removed from the dataset by requiring a close match with a bacterial rRNA secondary structure model (Nawrocki E P et al., Bioinformatics 2009; 25:1335-7). Sequences identified as potential chimeras by ChimeraSlayer software (Haas B J et al., Genome Res 2011; 21:494-504) were removed. The Ribosomal Database Project (RDP) Classifier software was used for taxonomic assignments (Wang Q et al., Appl Environ Microbiol 2007; 73:5261-7). Basic Local Alignment Search Tool (BLAST) database was used to assign species names to nearly identical sequences (Pruesse E et al., Nucleic Acids Res 2007; 35:7188-96). The taxonomic information was used to construct sequence groups with identical taxonomic rank and to identify specific bacteria differentially present between groups (Wagner B D et al., PLoS One 2011; 6:e20296). The taxonomic information was used to calculate ecology statistics for each sample. Bacterial load was determined based on 16s rRNA copy number. Based on gathered sequence and taxonomic information, dominant microbial communities in the airways of CR and CS asthmatics and normal controls were determined. Microorganisms were considered as expanded in asthma airway microbiome if they represented over 5% out of total 16s rRNA sequences and the % of sequences was increased at least 2 fold over controls for the organisms present both in the airways of asthmatics and normal control; for the Genera found only in asthma patients, microorganisms were considered as expanded if they represented over 5% of the total 16s RNA sequences.

Bacterial Cultures.

Haemophilus parainfluenzae (ATCC® number 9796™) and Prevotella melaninogenica (ATCC® number 25845™) were obtained from ATCC (Manassas, Va.) and cultured according to ATCC instructions. Haemophilus parainfluenzae (ATCC® number 9796™) and Prevotella melaninogenica (ATCC® number 25845™) for the cellular stimulation experiments were grown in brain heart infusion (BHI) media aerobically (H. parainfluenzae) or in pre-reduced anaerobically sterilized (PRAS) cooked meat glucose media at 37° C. under anaerobic conditions (P. melaninogenica). On the day of experiment bacterial concentration was calculated based on optical density (OD) at 620 nm and standard curves generated for each strain to determine the relationship between colony forming units (CFU) and OD. Bacteria were pelleted and resuspended in XVivo™ 15 (Lonza, Walkersville, Md.) culture media without antibiotics and added to the cells.

Cell Culture and Treatment.

Peripheral blood mononuclear cells (PBMC) were isolated from asthma patients. Monocytes were prepared by negative selection using Human Monocyte Isolation Kit II (Milteniyi Biotech Inc., Auburn, Calif.). BAL macrophages were enriched by 3h plastic adhesion. Cell purity was ≥95%. In all experiments, monocytes and BAL macrophages were cultured in the X-VIVO™ 15 serum free medium overnight; medium was replaced with X-VIVO™ 15 medium without antibiotics prior to addition of bacteria. Bacteria were added to 10$^6$ cells/ml in culture at 0.1 or 1 bacteria per cell.

Details about assessment of p38 mitogen activated protein kinase (MAPK) activation by bacteria in peripheral blood monocytes and BAL macrophages, effects of bacteria on cellular response to corticosteroids in vitro based on corticosteroid regulation of mitogen activated protein kinase 1 (MKP-1) and IL-8 mRNA expression, influence of selected pathway inhibitors on corticosteroid responses in the presence of bacteria and statistical data analyses are described below.

P38 Mitogen Activated Protein Kinase (MAPK) Stimulation by Bacteria.

P38 MAPK activation in response to various concentrations of pathogenic and commensal bacteria as well as time course of p38 activation in response to these bacteria was determined. Cells were stimulated with 0.1 and 1 bacteria per cell, at kinetic time frames from 15 min to 3h (monocytes), or after 3h of stimulation with bacteria (BAL macrophages). Cell lysates were prepared using the ice-cold complete lysis buffer (1× Cell Signaling Lysis Buffer, Cell Signaling Technology, Inc., Danvers, Mass.)) with 10 μL each PMSF, protease inhibitor cocktail, and sodium orthovanadate (Santa Cruz Biotechnology, Inc., Santa Cruz, Calif.) per 1 ml of lysis buffer). Protein concentration was determined by Bradford assay and cell lysates were analyzed for p-p38 MAPK expression by Western blot as described by us earlier (Zhang Y et al., *J Immunol* 2012, in press).

In Vitro Response to Corticosteroids in the Presence of Bacteria.

$0.5 \times 10^6$ monocytes or $2.5 \times 10^5$ BAL macrophages per condition were cultured overnight in X-VIVO™ 15 media, treated with 0.1 to 1 bacteria per cell or 10 ng/ml of *E. coli* strain 0111:B4 LPS (Sigma-Aldrich Corp) for 15 min and stimulated with $10^{-6}$ M dexamethasone (DEX) for an additional 3h still in the presence of bacteria. Following incubation the cells were preserved in RLT buffer (Qiagen, Inc., Valencia, Calif.). RNA was extracted using RNAEASY® Mini kit (Qiagen), and analyzed by real-time PCR as previously described (Goleva E et al., *J Allergy Clin Immunol* 2012; 129:687-93 e1) for the expression of corticosteroid-regulated targets mitogen activated kinase phosphatase 1 (MKP-1), and IL-8. 18s RNA was measured as a house keeping gene. All primers were purchased from Applied Biosystems (Life Technologies Corporation, Carlsbad, Calif.). Standard curves for gene targets were generated using the fluorescent data from two-fold serial dilutions of total RNA of the highest expression sample. Quantities of each target gene in test samples were normalized to the corresponding levels of the housekeeping gene (18s RNA) in each sample. Fold induction and fold suppression by DEX of selected gene targets was calculated for cells cultured in media, with LPS or with bacteria.

The Effects of Inhibitors on Cellular Response to Corticosteroids.

To examine whether MAPK inhibition or transforming growth factor beta associated kinase 1 (TAK1) inhibition reverses the corticosteroid resistant response to pathogenic microbes, monocytes were pretreated with either TAK1 inhibitor (5Z)-7-Oxozeaenol, *Curvularia* sp. (Calbiochem, E M D Serono, Inc., Rockland, Mass.) (2 μM), the p38 inhibitor, SB203580 (10 mM) (Calbiochem) or the cocktail of the three MAPK inhibitors (SB203580, p38 inhibitor; PD98059, MEK1/ERK inhibitor (Invitrogen, Life Technologies, Grand Island, N.Y.) and SP600125, JNK inhibitor (InVivogen, San Diego, Calif.), all at 10 μM) for 1h prior to stimulation with bacteria and cellular response to corticosteroids was evaluated by real time PCR as described above. To assess the efficacy of inhibitors on suppression of cell activation induced by bacteria cells were pretreated with inhibitors for 1h or cultured in media, stimulated with *H. parainfluenzae* for 15 min. Protein lysates were prepared as described above. ERK and hsp27 phosphorylation as downstream targets for TAK1 and p38 MAPK activation, respectively, were assessed by Western blot as described in (Zhang Y et al., *J Immunol* 2012, in press; Li L B et al., *J Allergy Clin Immunol* 2004; 114:1059-69; Zhang Y et al., *J Biol Chem* 2009; 284:24542-52).

Statistical Analysis.

Descriptive statistics (mean and standard deviation, median and inter quartile range) were generated. ANOVA (comparison between normal controls, CR and CS asthmatics), unpaired t-test (comparison between normal controls and asthmatics; comparison between CR and CS asthma groups) and paired t-test (pairing by experimental treatment conditions, i.e. bacterial stimulation vs media treatment; media treatment vs DEX treatment; treatment with and without inhibitor) or non-parametric tests were used for data analysis. Non-parametric test were applied if the data were not normally distributed. Statistical analysis was performed using JMP® version 10 (SAS® Institute, Cary, N.C.) and GraphPad Prism, version 5 (GraphPad Software, La Jolla, Calif.). Differences were considered significant at p<0.05. A minimum of three independent experiments was conducted to allow for statistical comparisons.

Example 1

This example shows the airway microbiome in asthmatics.

Bacterial 16s rRNA gene sequencing from BAL samples of 39 adult asthmatics and 12 healthy controls was performed (FIG. 1A). No significant differences in airway bacterial load were observed between asthmatics and normal controls (FIG. 1B). Alterations in the airway microbiome composition were noted in asthmatics, as compared to controls, with a significant reduction of the airway commensals genera *Prevotella* and *Veillonella* (p<0.05), reduction in phylum Fusobacteria (p<0.05) and expansions of phyla Actinobacteria (p<0.01) and Proteobacteria (FIG. 1A).

Figure 1C:
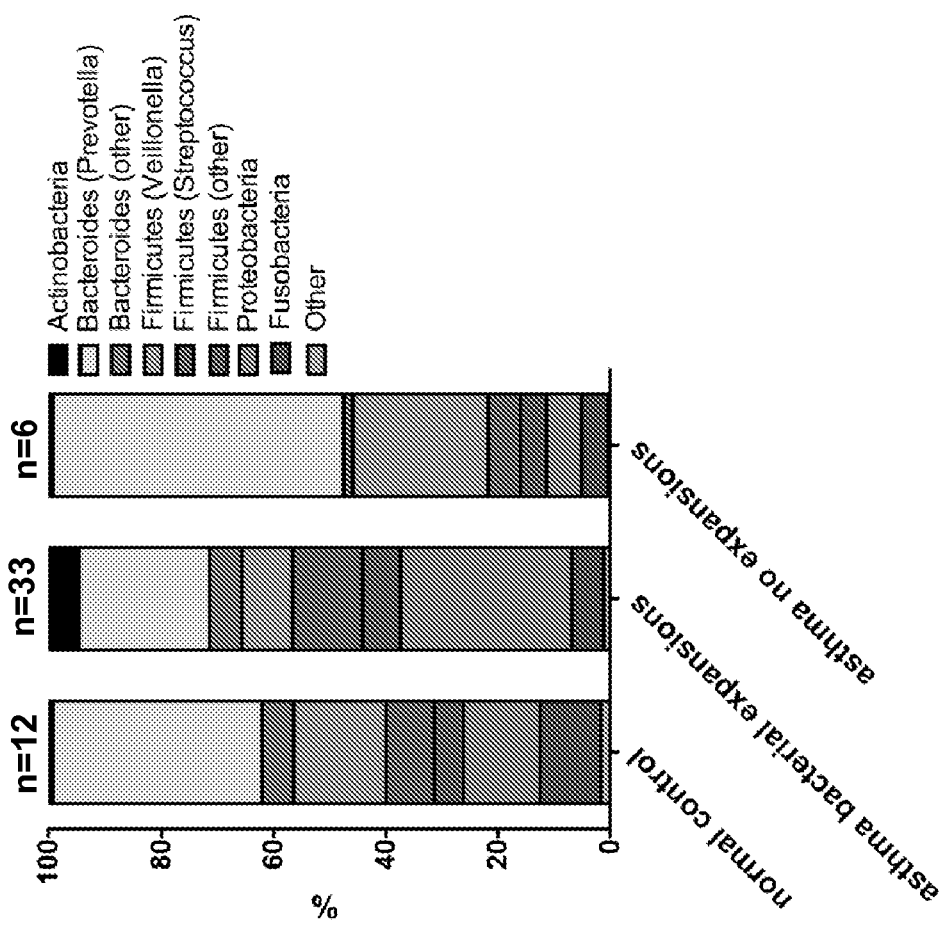
Figure 1E:
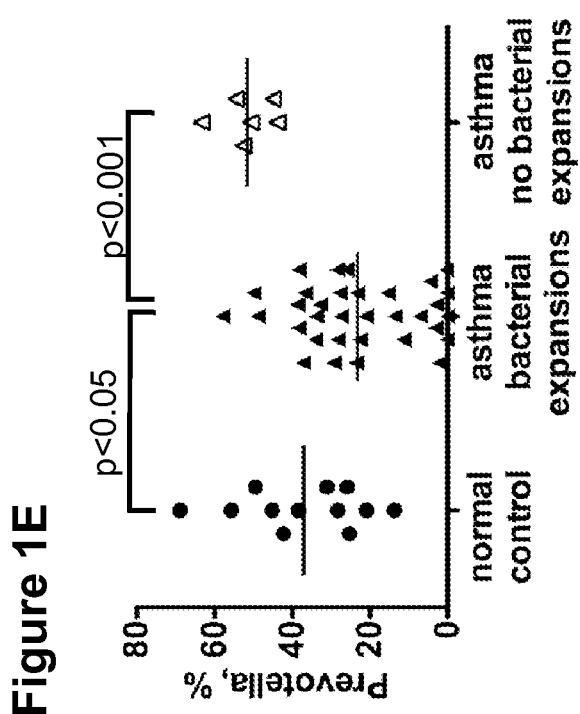
Figure 1F:
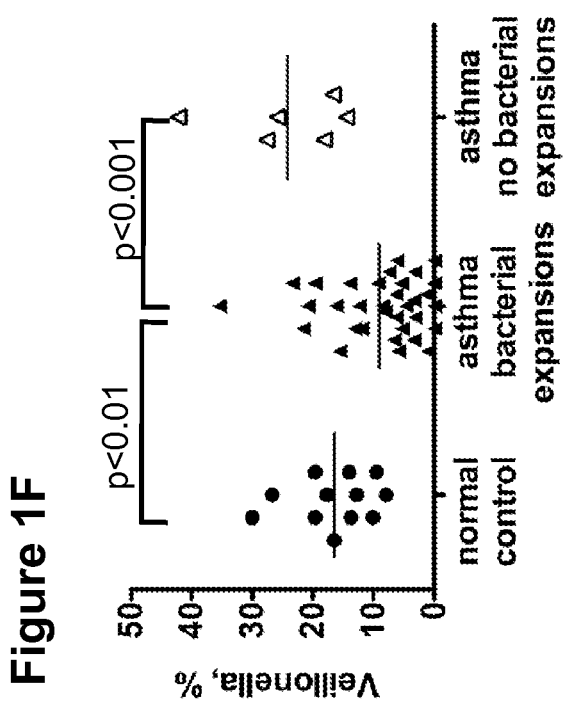
Figure 1G:
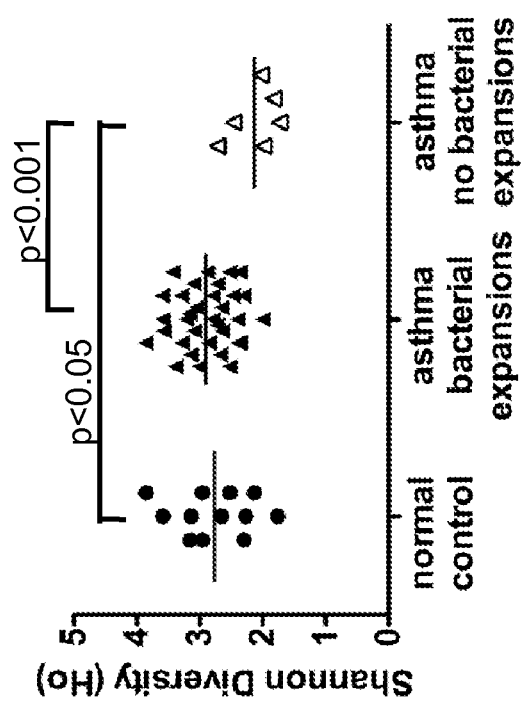

Normal controls were used to establish the normal distribution of the major taxonomic groups of bacteria in the airways. Compared to normal controls, 33 asthmatics out of 39 asthmatics studied had expansions of specific groups of microorganisms (>5% of 16s rRNA sequences, at least 2-fold above normal controls or organisms not found in normals) (FIG. 1C). Despite similar airway bacterial load to normal controls (as shown by 16s RNA copy number (FIG. 1D)), both groups of asthmatics (with bacterial expansions and with no bacterial expansions) had significant alterations in the lung microbiome composition (FIG. 1C). Asthmatics with bacterial expansions had a significant reduction in the number of sequences of airway commensals, genera *Prevotella* and *Veillonella*, (p<0.05 and p<0.01 as compared to normal controls for the % of *Prevotella* and *Veillonella* sequences, respectively) (FIG. 1D, 1E). Instead, these patients had significant expansions of phyla Actinobacteria and Proteobacteria (p<0.01 and p<0.05 as compared to normal controls, respectively) (FIG. 1C). In contrast, asthmatics with no bacterial expansions (n=6) had significantly increased % sequences for genera *Prevotella* and *Veillonella* (p<0.001 and p<0.001 as compared to asthmatics with bacterial expansions), but depleted other bacterial families as shown by significantly reduced bacterial diversity compared to normal controls (p<0.05) and asthma patients with bacterial expansions (p<0.001) (FIG. 1D-1F).

Example 2

This example demonstrates that a subset of CR asthmatics has unique bacterial expansions in their airways.

In this study all asthma patients were evaluated for clinical response to corticosteroids based on oral prednisone burst. Twenty-nine asthmatics were categorized as resistant to corticosteroids (CR), ten patients were categorized as corticosteroid sensitive (CS) (ΔFEV1% after oral prednisone burst was −0.2±5.9% and 31.0±23.5% for CR and CS asthma groups, respectively, p<0.0001 (Table 2)).

Figure 2:
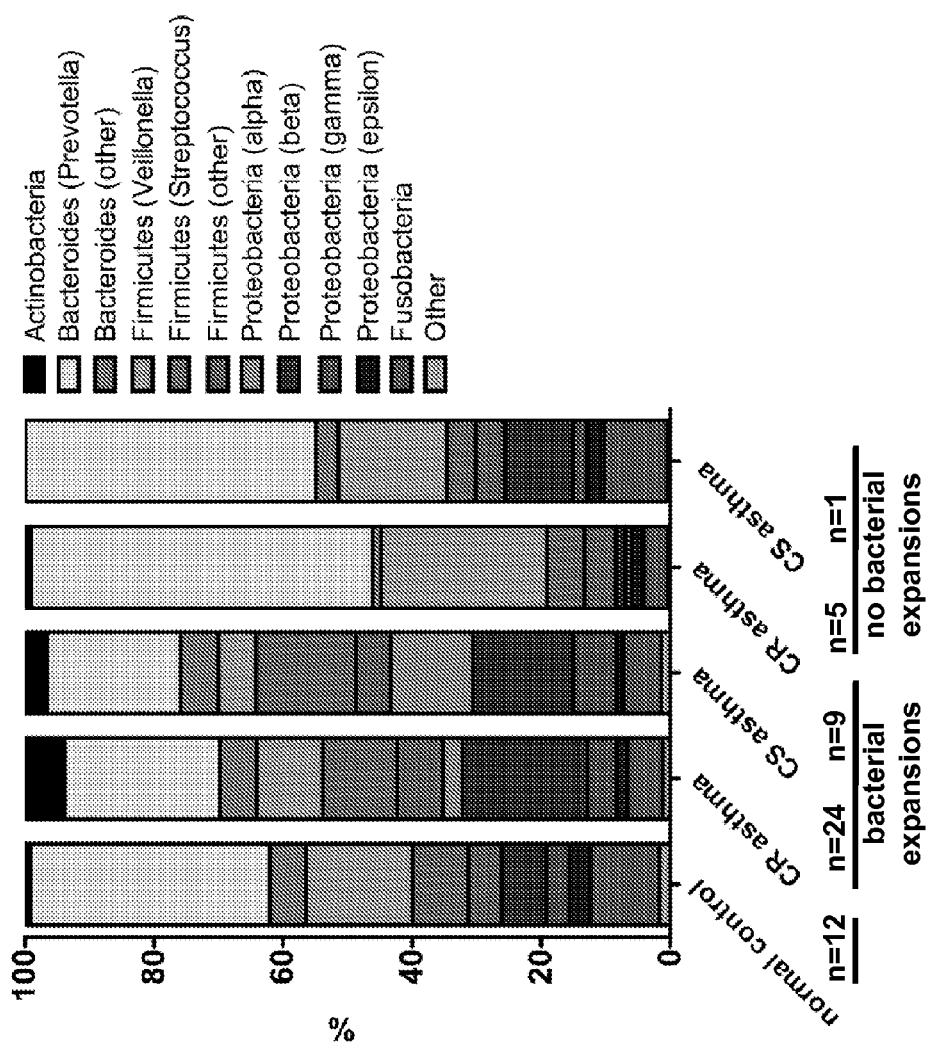
FIG. 2 shows the composition of the airway microbiome in normal controls and CR and CS asthma patients with and without bacterial expansions. A mean % of major bacterial phyla per group is shown.

Microbiome analysis revealed that majority of CR asthmatics (24 out of 29 patients) and CS asthmatics (9 out of 10 patients) had microbial expansions (FIG. 2). Details of bacterial expansions in the airway microbiome of CR and CS asthmatics are summarized in the Table 1.

Figure 5A:
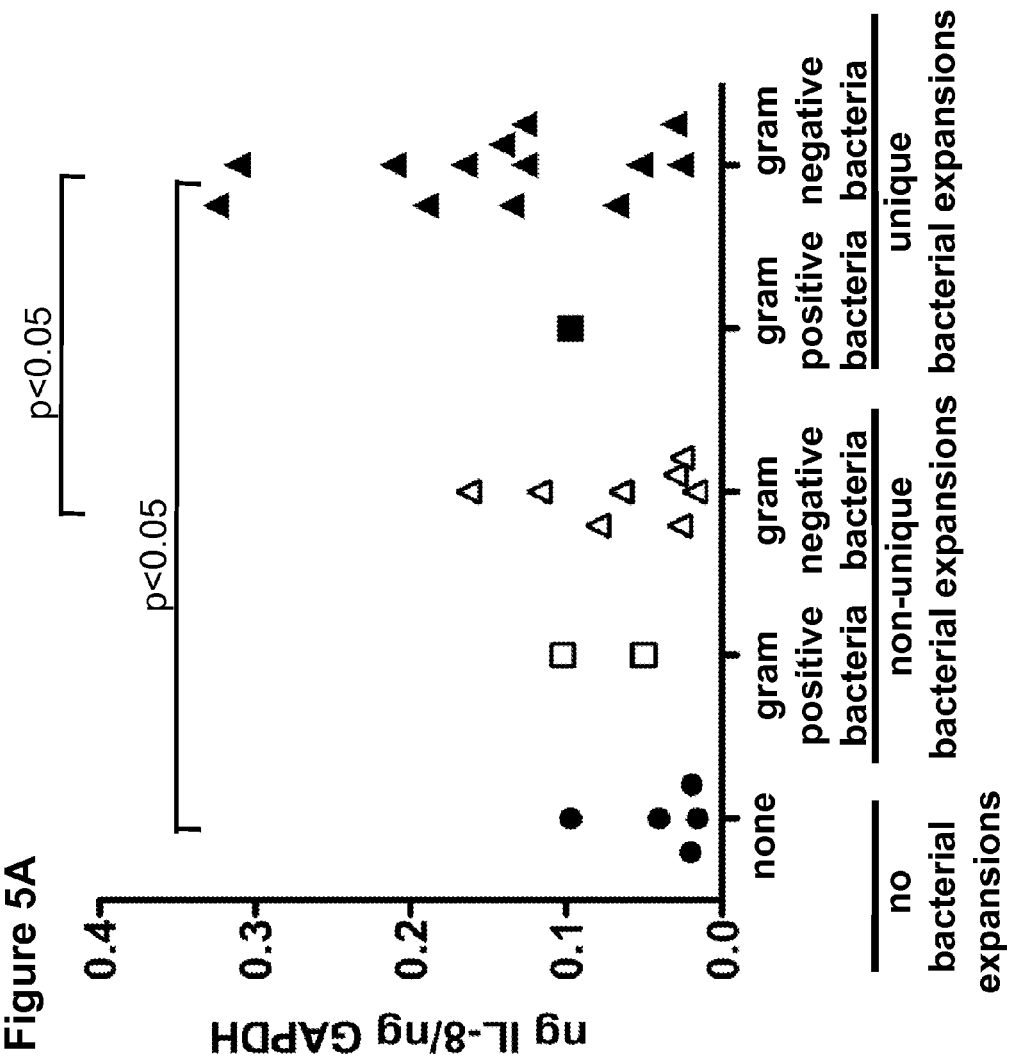

Fourteen CR asthmatics had unique bacterial expansions in the airways that were not expanded in CS asthmatics (Table 1). The distinct bacteria expanded in the airways of CR asthmatics were mainly gram-negative organisms (Table 1). BAL cells of CR asthmatics with unique gram-negative bacteria expansions expressed significantly higher levels of IL-8 mRNA (p<0.05 compared to BAL cells from CR asthmatics with no bacterial expansions or CR asthmatics with gram-negative bacteria expansions that are common between CR and CS asthmatics) (FIG. 5A). Importantly, these patients had significantly higher LPS levels in BAL fluid (p<0.05) (FIG. 5B).

Example 3

This examples shows the effects of microbiome on cell activation and response to corticosteroids in airway macrophages.

Haemophillus parainfluenzae was chosen, one of the microorganisms from Proteobacteria phylum, uniquely expanded in the airways of CR asthmatics, to examine the effects of this microorganism on cellular responses to corticosteroids. The effects of H. parainfluenzae were compared to the airway commensal organism, Prevotella melaninogenica. As the numbers of BAL macrophages from asthmatics were limited, the interactions of these microbes with peripheral blood monocytes were initially assessed, and then applied developed protocols to assess BAL macrophages interactions with these bacteria. As shown in FIG. 6, H. parainfluenzae, but not P. melaninogenica, induced a dose-dependent and time-dependent activation of the p38 MAPK pathway, which persisted even after 3h since addition of H. parainfluenzae (FIG. 6). Cells cultured with H. parainfluenzae had significantly reduced responses to corticosteroids (FIG. 6).

Figure 3A:
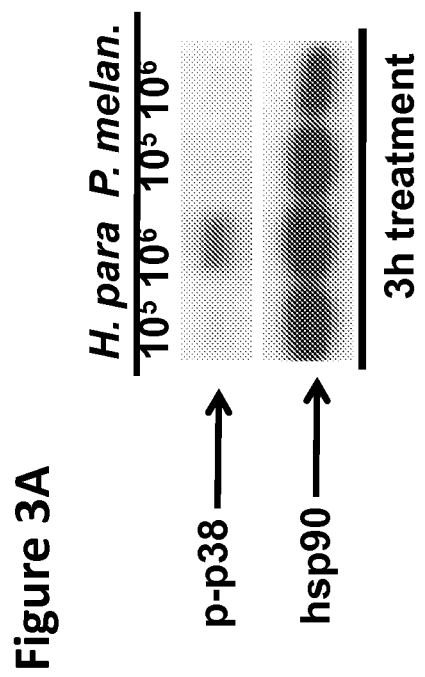
FIGS. 3A-3D show the effects of bacteria from the airways of asthmatics on BAL macrophages activation and response to corticosteroids in vitro. Incubation of asthmatic BAL macrophages with *H. parainfluenzae* (H para) results in p38 MAPK activation in the cells as detected by Western blot (FIG. 3A); upregulation of IL-8 (FIG. 3B) and MKP-1 mRNA production (FIG. 3C) and reduced responsiveness to corticosteroids in vitro (FIG. 3D) as shown by real time PCR. Cells cultured with airway commensal organism *P. melaninogenica* (*P. melan*) do not activate p38, do not upregulate IL-8 mRNA and MKP-1 mRNA expression and remain sensitive to corticosteroid treatment. For IL-8 mRNA and MKP-1 mRNA production the cells were cultured overnight in X-VIVO™ 15 medium, incubated with bacteria for 15 min followed by 3h of treatment with $10^{-6}$M dexamethasone (DEX) or medium and analyzed by real time PCR (FIGS. 3B, 3C and 3D). Bacteria were added to $0.25 \times 10^6$ cells per condition (bacteria to cell ratio 0.1:1 and 1:1). The responses of BAL macrophages from 5 asthmatics were examined. *$p<0.05$, **$p<0.01$ as compared to medium treated cells.
Figure 3B:
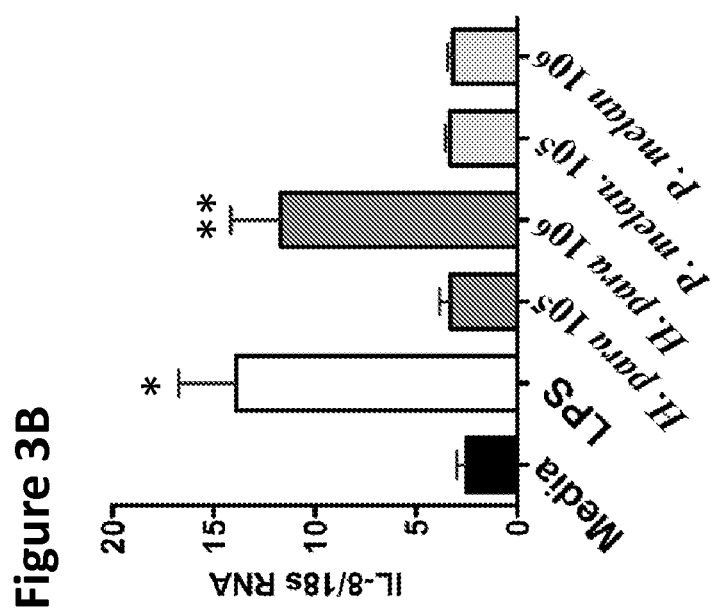
Figure 3C:
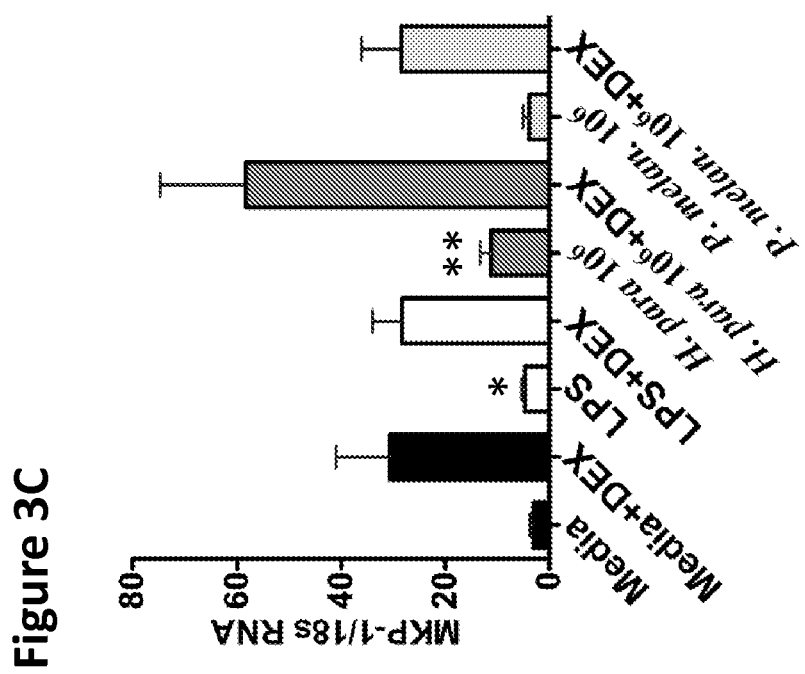
Figure 3D:
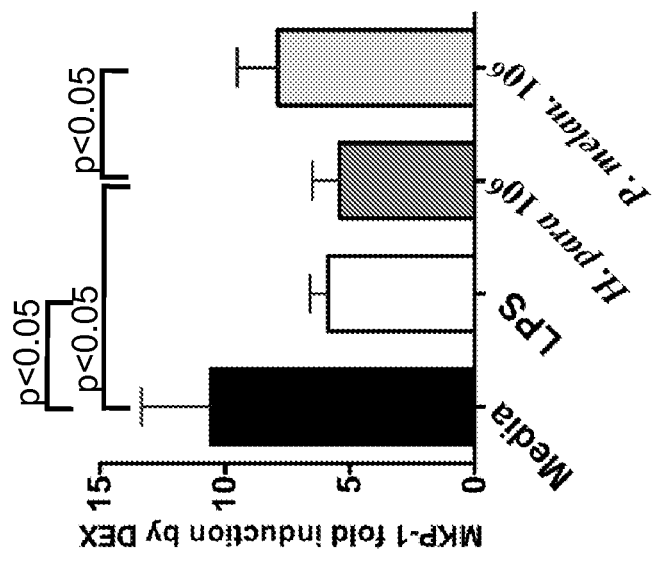

P38 MAPK activation in asthmatic BAL macrophages was only observed in response to H. parainfluenzae, but not P. melaninogenica, after 3h of stimulation (FIG. 3A). H. parainfluenzae, but not P. melaninogenica significantly upregulated IL-8 mRNA (FIG. 3B) and MKP-1 mRNA (FIG. 3C) expression by BAL macrophages. In the presence of H. parainfluenzae MKP-1 induction by dexamethasone (DEX) was significantly reduced (FIG. 3D) (p<0.05). BAL cells remained steroid sensitive in the presence of P. melaninogenica (FIG. 3D).

Example 4

This examples shows the effects of MAPK and transforming growth factor beta associated kinase-1 (TAK1) inhibitors on cellular responses to corticosteroids in the presence of H. parainfluenzae.

Toll-like receptor (TLR) engagement by bacteria is the major pathway of cell activation by bacteria (Akira S, Nat Rev Immunol 2004; 4:499-511). TAK1 phosphorylation represents a key downstream TLR signaling branching point that controls both MAPK and NFkB pathway activation in the cells (Liew F Y et al., Nat Rev Immunol 2005; 5:446-58). To address the role of TLR signaling pathways in MAPK and TAK1 activation by H. parainfluenzae and the alteration of cellular response to corticosteroids, asthmatic peripheral blood monocytes were preincubated with/without TAK1 and MAPK inhibitors for 1 hour, stimulated with bacteria followed by treatment with DEX or medium and analyzed by real time PCR.

Figure 4B:
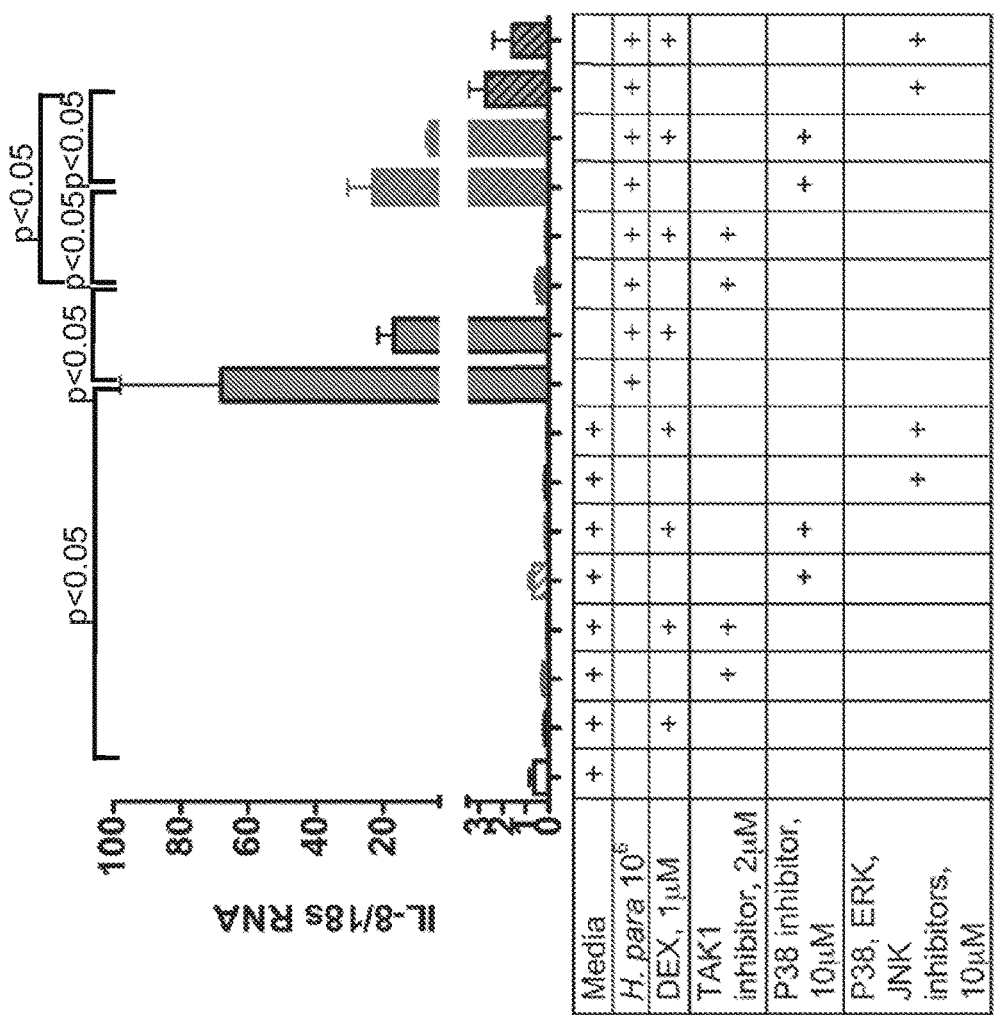
Figure 4C:
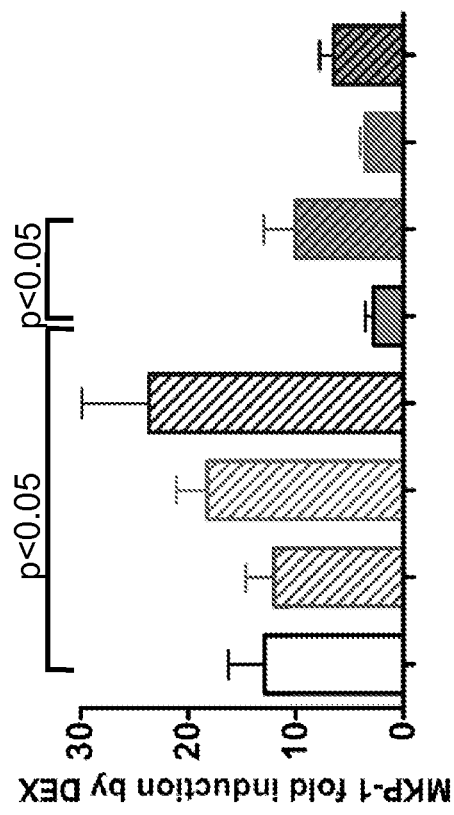
Figure 4D:
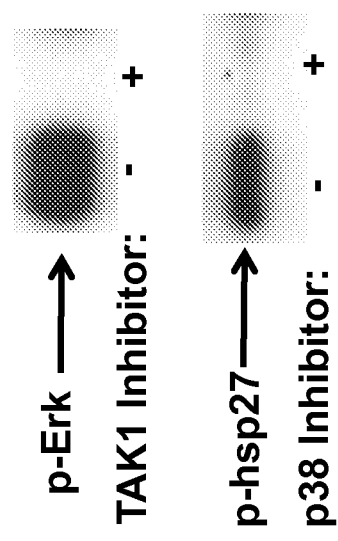

Peripheral blood monocytes from asthmatics cultured in the presence of H. parainfluenzae had significant upregulation in MKP-1 mRNA (p<0.05) (FIG. 4A) and IL-8 mRNA (p<0.05) (FIG. 4B) production. Cells cultured with H. parainfluenzae had reduced responses to corticosteroids as shown by significant inhibition of MKP-1 mRNA induction by DEX (FIG. 4C). Pretreatment of monocytes with the TAK1 inhibitor resulted in significant inhibition of MKP-1 mRNA (FIG. 4A) and IL-8 mRNA (FIG. 4B) induction by H. parainfluenzae and restoration of cellular sensitivity to corticosteroids in vitro (FIG. 4C). P38 MAPK inhibitor and p38 MAPK/ERK/JNK inhibitors combo also reduced MKP-1 mRNA and IL-8 mRNA induction by H. parainfluenzae, but not as effective as TAK1 inhibitor (FIG. 4A, 4B). P38 and MAPK inhibitors combo failed to restore cellular sensitivity to corticosteroids in the presence of H. parainfluenzae (FIG. 4C). As shown by Western blot the doses of inhibitors used were sufficient in inhibition of cell activation via pathways that they target, as 2 µM TAK1 inhibitor and 10 µM p38 MAPK inhibitor fully inhibited activation of ERK and hsp27 phosphorylation by H. parainfluenzae as a downstream read out targets for TAK1 and p38 MAPK activation, respectively (FIG. 4D).

Example 5

This example shows peripheral blood monocytes activation and response to corticosteroids in the presence of bacteria identified in airways of asthmatics.

Figure 6A:
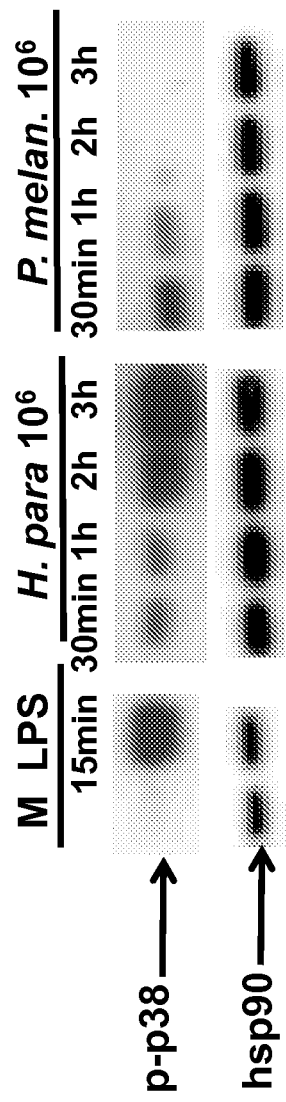
FIGS. 6A-6F shows the effects of bacteria from the airways of asthmatics on peripheral blood monocytes activation and response to corticosteroids in vitro. Incubation of asthmatic peripheral blood monocytes with *H. parainfluenzae* (*H. para*) results in p38 MAPK activation (FIGS. 6A, 6B) in the cells as detected by Western blot; upregulation of IL-8 and MKP-1 mRNA production (FIGS. 6C, 6E) and reduced responsiveness to corticosteroids in vitro (FIGS. 6D, 6F) as shown by real time PCR. Cells cultured with airway commensal organism *P. melaninogenica* (*P. melan*) poorly activate p38 but do not upregulate IL-8 mRNA and MKP-1 mRNA expression and remain sensitive to corticosteroid treatment. For IL-8 mRNA and MKP-1 mRNA production the cells were cultured overnight in serum-free hematopoietic cell medium (X-VIVO™ 15 media, Lonza, Walkersville, Md.), incubated with bacteria for 15 min followed by 3h of treatment with $10^{-6}$M DEX or media and analyzed by real time PCR (FIGS. 6C-6F). Bacteria were added to $0.5 \times 10^6$ cells per condition (bacteria to cell ratio 0.1:1 and 1:1). The responses of monocytes from 7 asthmatics were examined. *$p<0.05$, $p<0.01$, *$p<0.001$ as compared to media treated cells
Figure 6B:
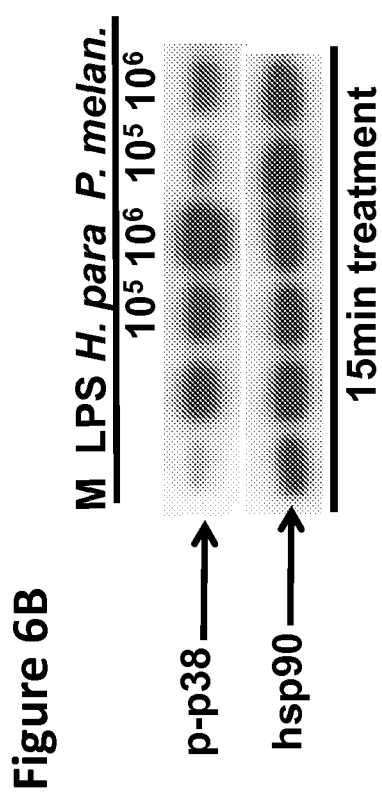
Figure 6C:
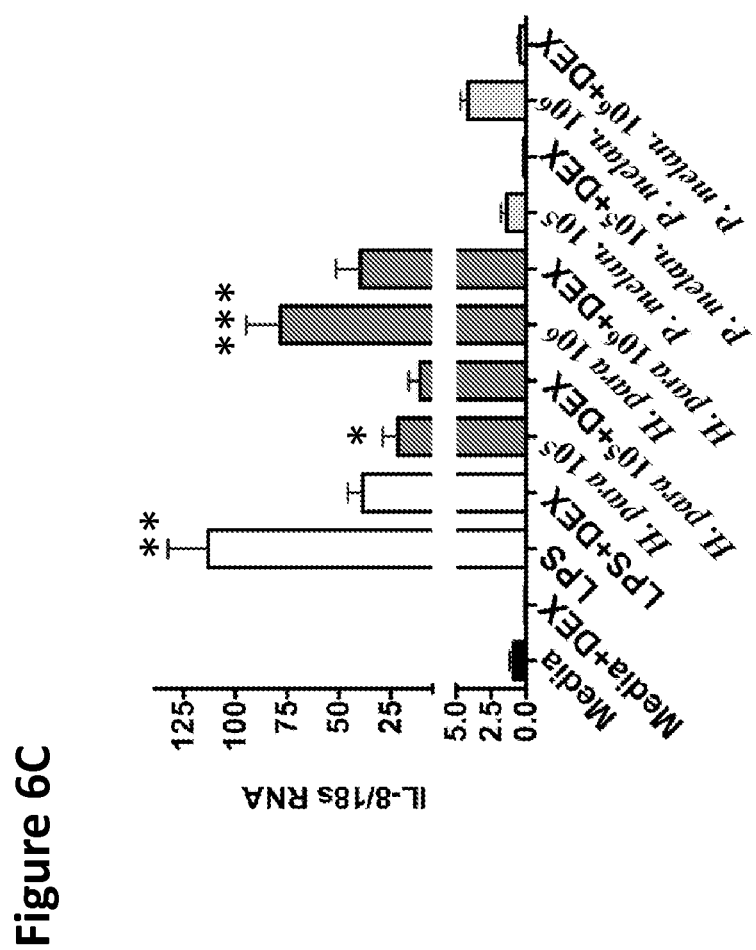
Figure 6D:
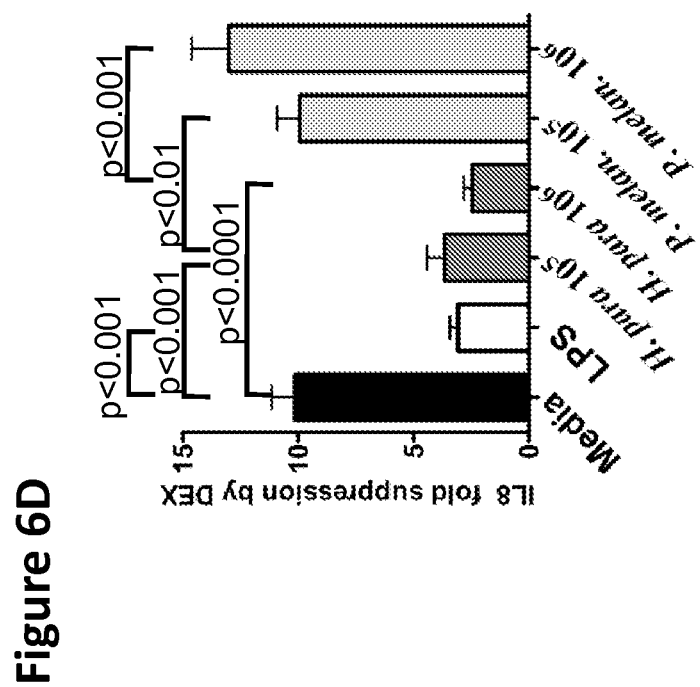
Figure 6E:
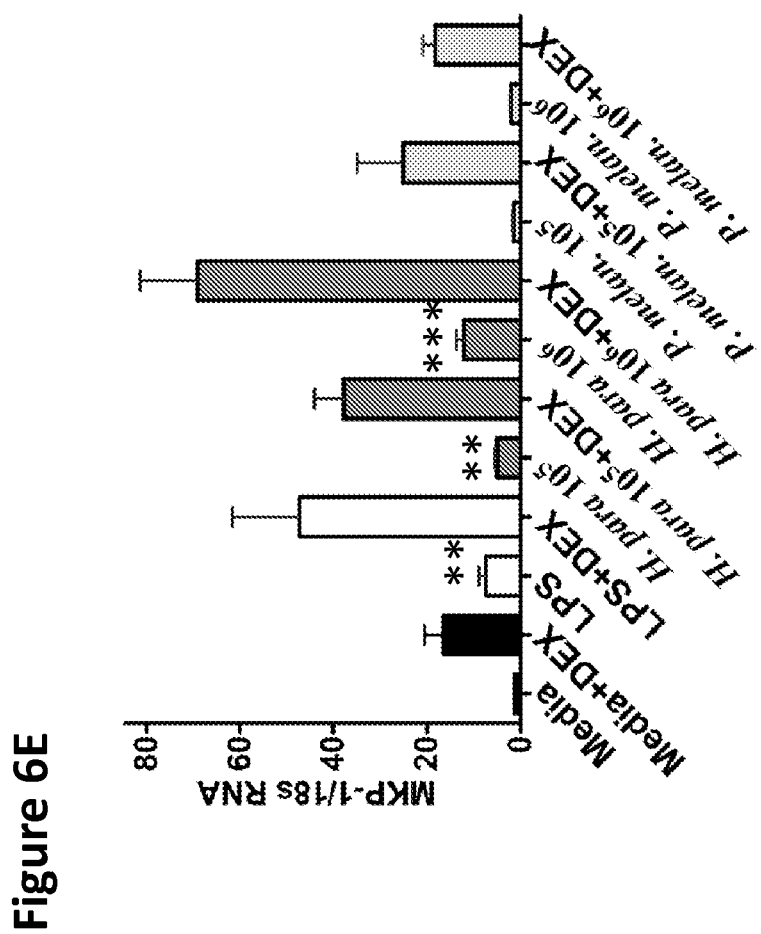

Preincubation of monocytes from asthmatics with H. parainfluenzae resulted in p38 MAPK activation (FIG. 6A,6B) and significant upregulation of the IL-8 mRNA (FIG. 6C) and MKP-1 mRNA (FIG. 6E). Stimulation with H. parainfluenzae inhibited monocyte response to corticosteroids, as shown in significantly reduced IL-8 mRNA suppression by DEX (FIG. 6D) (p<0.001 and p<0.001 comparing IL-8 fold suppression by DEX in cells cultured in the presence of $10^5$ H. parainfluenzae vs media or cells cultured in the presence of $10^6$ H. parainfluenzae vs media, respectively) and MKP-1 mRNA induction by DEX (FIG. 6F) (p<0.001 and p<0.0001 comparing MKP-1 fold induction by DEX in cells cultured in the presence of $10^5$ H. parainfluenzae vs media or cells cultured in the presence of $10^6$ H. parainfluenzae vs media, respectively).

Figure 6F:
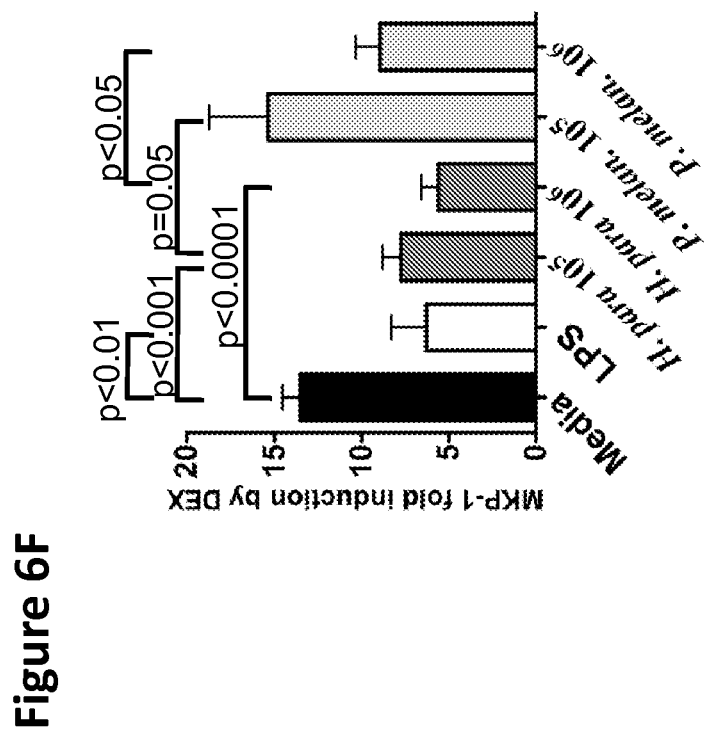

In contrast, when the monocytes were preincubated with commensal organism from the airways, P. melaninogenica, the cells had poor p38 MAPK activation (FIG. 6A, 6B), which did not result in upregulation of IL-8 mRNA and MKP-1 mRNA (FIG. 6C, 6E) and the cells remained steroid sensitive similar to steroid responses of cells that were cultured without bacteria (FIG. 6D, 6F).

A time course of p38 MAPK activation in monocytes (FIG. 6A) demonstrated increased p38 activation in response to *H. parainfluenzae* and *P. melaninogenica* after 15 min of stimulation, which was sharply increased in response to *H. parainfluenzae* and diminished in response to *P. melaninogenica* by 3h after stimulation. Response to *H. parainfluenzae* and *P. melaninogenica* was found to be dose dependent, but corresponding doses of *P. melaninogenica* were always less stimulatory as compared to *H. parainfluenzae*. Cellular steroid response was reduced in the presence of *E. coli* LPS, which was used as a positive control in these experiments (FIG. 6).

Airway Microbiome Findings in Asthmatics:

Patients evaluated in this study remained symptomatic as reflected by the ACQ score. It is possible that lack of response to steroids in the host allows such microbial expansions as persistent inflammation may impair host defense, which deserves further evaluation. Selective expansions of microorganisms was not observed in patients that were treated with ICS at the time of evaluation as opposed to patients that were not on ICS.

Recent literature suggests that commensal microbiota maintains and shapes normal mucosal immunity in the gut (Ivanov, I I et al., *Curl. Opin Microbiol* 2011; 14:106-14; Artis D, *Nat Rev Immunol* 2008; 8:411-20). Similarly, it has been reported that *Staphylococcus epidermidis*, a commensal organism in the skin, can protect the host from development of injurious inflammation by tolerizing the response via TLR (Lai Y et al., *Nat Med* 2009; 15:1377-82). By analogy, it is possible that commensal microbiota in the airways is protective from development of inflammatory responses; and loss of commensal organisms allows cellular inflammatory response. Restoration of the commensal microbiota in the airways of asthmatics should be evaluated for its protective role and alleviation of cellular steroid response in the airways of asthmatics, such as those with chronic rhinosinusitis. It has been shown recently that sinus microbiota of patients with chronic rhinosinusitis exhibits significantly reduced bacterial diversity compared with that of healthy controls (Abreu N A et al., *Sci Transl Med* 2012; 4:151ra24). Multiple, phylogenetically distinct lactic acid bacteria were depleted concomitant with an increase in the relative abundance of a single species, *Corynebacterium tuberculostearicum* (Abreu N A et al., *Sci Transl Med* 2012; 4:151ra24). In a murine model of rhinosinusitis *Lactobacillus sakei*, a commensal organism from the sinuses, defended against *C. tuberculostearicum* sinus infection, even in the context of a depleted sinus bacterial community (Abreu N A et al., *Sci Transl Med* 2012; 4:151ra24).

It was shown recently that the composition of BAL bacterial communities in healthy controls is similar but lower in burden then those from upper airways of these subjects (Charlson E S et al., *Am J Respir Crit Care Med* 2011; 184:957-63). Whether such findings reflect contamination during lower airway sampling by upper airway microbiota, or low-level colonization via inhalation or microaspiration of organisms into the lower airways requires further studies. In the inventors study comparison of bacterial 16s rRNA gene sequences between five matching BAL samples and oropharyngeal swabs demonstrated only marginal overlap (Mean±SD, 62±36%) similarity based on the Morisita-Horn beta diversity analysis). Some of the microorganisms that were found expanded in the airways of asthmatics are not typical representative of the upper airway microbiota. But it is possible that they were acquired from patients' environment, and then "trapped" in the lower airways due to failed clearance.

Materials and Methods for Examples 6-9

Patients 26 adult asthma patients were enrolled. Sample collection involved assessment of patients with a clinical history of asthma, airflow limitation (baseline $FEV_1$ 85% predicted) and either airway hyperresponsiveness ($PC_{20}$ methacholine <8 mg/ml) or bronchodilator responsiveness (>12% improvement in $FEV_1$% predicted after 180 mg metered-dose inhaler albuterol). Corticosteroid response of asthmatics was classified based on their prebronchodilator morning $FEV_1$% predicted response to one week course of 40 mg/d oral prednisone. Asthmatics were defined as SR (steroid resistant) if they had less than 10% improvement in FEV1 and steroid sensitive (SS) if they showed significant improvement (≥12%). Subject characteristics are presented in Table 4.

TABLE 4

Patient characteristics

|  | SR asthma n = 12 | SS asthma n = 13 |
|---|---|---|
| Age, yrs, (Mean ± SE) | 37.2 ± 3.3 | 39.2 ± 3.0 |
| Gender (Male/Female) | 6/6 | 3/10 |
| Race (C/AA/Other) | 7/4/1 | 11/0/2 |
| BMI, kg/m², (Mean ± SE) | 28.5 ± 2.0 | 30.7 ± 2.4 |
| IgE, U/ml, (Mean ± SE) | 240 ± 95 | 129 ± 25 |
| Baseline $FEV_1$ % predicted, (Mean ± SE) | 78.2 ± 2.5* | 59.8 ± 5.3 |
| $FEV_1$ % reversal with Albuterol, (Mean ± SE) | 13.3 ± 2.1* | 41.1 ± 8.7 |
| $FEV_1$ % change after Prednisone burst, (Mean ± SE) | 0.8 ± 1.9** | 42.2 ± 10.0 |
| Corticosteroid medications*** |  |  |
| ICS/LABA | 4 | 4 |
| ICS | 3 | 3 |
| none | 5 | 6 |

*$p < 0.01$;
**$p < 0.0001$ as compared to SS asthmatics
***For the SR and SS asthmatics that received ICS/LABA or ICS the Mean ± SE of the ICS dose in budesonide equivalents was 1137 ± 410 µg and 1217 ± 398 µg, respectively.

Reagents and Antibodies

PHOSFLOW™ Lyse/Fix buffer, PHOSFLOW™ Perm/Wash Buffer I and Stain Buffer were purchased from BD Pharmingen (San Diego, Calif.). Primary fluorophore-conjugated antibodies specific to phosphorylated proteins p38 MAPK (pT180/Y202) Alexa 647 and p44/42 MAPK (pT201/Y202) Alexa 647, mouse IgG1 Alexa 647 were purchased from BD Pharmingen (San Diego, Calif.); JNK/SAPK Alexa 647 was from Cell Signaling Technology (Beverly, Mass.). Fluorophore-conjugated antibodies against cell-specific surface proteins: CD3 FITC, CD4 PE, CD8 PerCp-Cy5.5, CD14 FITC, CD16 PE, CD20 PerCp, were purchased from BD Pharmingen. Anti-total and phospho-p38 MAPK, p44/42 MAPK, JNK/SAPK and MSK1 antibodies, as well as anti-Hsp90 antibody were purchased from Cell Signaling Technology.

BAL Macrophages and PBMC Preparation

Fiberoptic bronchoscopies with bronchoalveolar lavage (BAL) were performed. BAL cells cytospins were prepared. The cytospins were stained with anti-phospho-ERK, phospho-p38 and phospho-JNK rabbit monoclonal antibodies (Cell Signaling Technology) followed by incubation with cy3-labeled donkey anti-rabbit IgG (Jackson ImmunoResearch Laboratories, West Grove, Pa.) to detected p-MAPK positive cells. Cell nuclei were counterstained with DAPI nuclei stain.

Heparinized peripheral blood was collected from all study subjects. PBMC were isolated by FICOLL-HYPAQUE® density gradient centrifugation. Isolated cells were resuspended at $1 \times 10^6$ cells/ml in RPMI 1640 medium containing 10% charcoal-filtered fetal calf serum (FBS; Gemini Bio-Products, Calabasas, Calif.).

Cell Surface and Intracellular Phospho-MAPK Flow Cytometry Analysis

300 µl of blood was fixed in 6 ml of BD PHOSFLOW™ Lyse/Fix buffer at 37° C. for 10 min and then washed once with 6 ml PBS. After centrifugation, the cell pellet was permeabilized in 3 ml of BD PHOSFLOW™ Perm/Wash Buffer I for 10 min at room temperature. Cell pellet was resuspended in 200µl of staining buffer, and cell suspension was equally divided between four FACS tubes containing 50 µl of monoclonal antibodies (CD surface antibodies plus anti-p-MAPK or isotype control). Cells were incubated at room temperature for 45 min in the dark. After the final wash, cells were resuspended in 1% paraformaldehyde (200 µl) and stored at 4° C. Cells were examined using FAC-SCALIBER™ (San Jose, Calif.) and data were analyzed using CELLQUEST™ software.

Western Blot

Whole cell extracts were prepared from freshly isolated PBMC, fifty micrograms of protein per condition were run on a 4-25% gradient gel (Bio-Rad Laboratories, Hercules, Calif.) and transferred to nitrocellulose membranes. The membranes were blotted with 1:1000 primary antibodies overnight at 4° C. After serial washes with TBS containing 0.1% Tween20, membranes were incubated with appropriate peroxidase-conjugated secondary antibodies for 1 h at RT. Immunoreactive bands were visualized using a chemiluminescent kit (GE Healthcare) and images were captures on film (GE Healthcare). Developed X-ray films were scanned and densitometry of the bands was quantified with NIH Image software (version 1.63). Hsp90 detection was used to control the quality of protein preparation and to ensure that equal amounts of cellular proteins were loaded per lane.

Real-Time PCR

Total RNA from freshly isolated SR and SS asthma patients PBMC was prepared using RNEASY® Mini kit (Qiagen, Valencia, Calif.). After reverse transcription, 500 ng cDNA from each sample were analyzed by real-time PCR using the dual-labeled fluorogenic probe method on an ABI PRISM® 7300 real time PCR system (APPLIED BIOSYSTEMS®). The expression of human IL-6 mRNA and 18s RNA was determined. All primers were purchased from Applied Biosystems APPLIED BIOSYSTEMS® (Foster City, Calif.).

Measurement of LPS in BAL Fluid

The content of LPS in BAL fluid was analyzed by using the chromogenic limulus amebocyte lysate (LAL) test (Cambrex Bio Science Walkersville, Inc, Walkersville, Md.), according to the manufacturer's instructions and normalized to the total protein level in each sample.

Statistical Analysis

Results were expressed as the Mean±SE. Statistical analysis was conducted using GraphPad Prism, version 5 (GraphPad Software, La Jolla, Calif.). The data were analyzed by the unpaired Student's t test. Differences were considered significant at $p<0.05$.

Example 6

This example shows MAPK phosphorylation in BAL macrophages of asthmatics.

Figure 7:
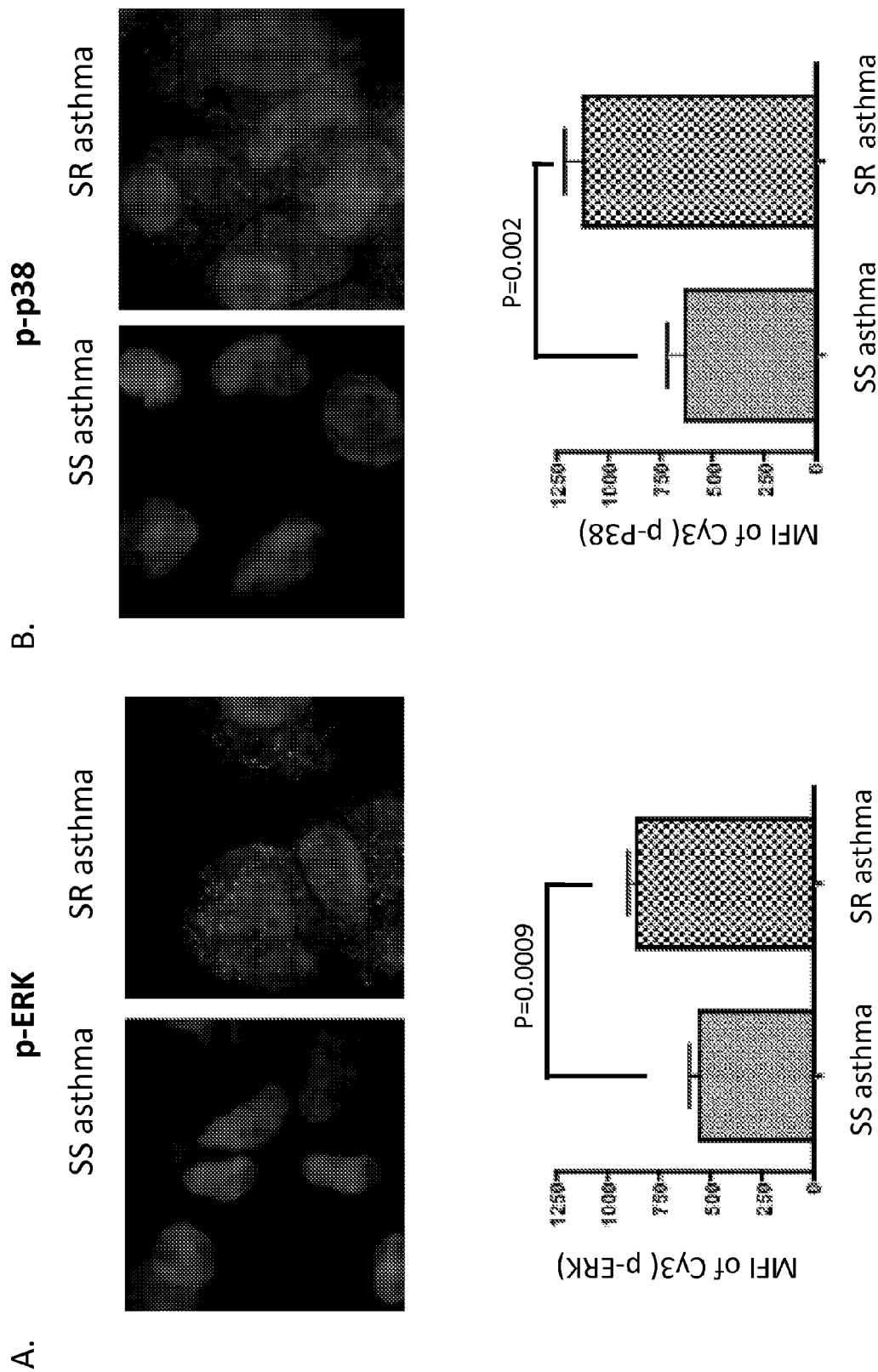
FIGS. 7A-7B show increased expression of p-MAPKs in BAL macrophages of subjects with SR asthma. Significantly increased p-ERK (FIG. 7A) and p-p38 (FIG. 7B) expression in BAL macrophages of SR asthmatics. Representative images of p-ERK and p-p38 in BAL macrophages in SR and steroid sensitive (SS) asthmatics are shown (original magnification, ×630; darker areas, DAPI-nuclear staining; spotted areas, cy3-p-ERK or p-p38). The MFI of p-ERK and p-p38 staining in BAL macrophages (FIG. 7B). MFI in 50 macrophages were analyzed for each study subject.

Phosphorylation of MAPKs in BAL macrophages from asthmatics was examined by immunofluorescence staining of BAL cell cytospins. BAL cytospins analyzed mainly consisted of macrophages (>90% cells). Among the subjects tested, the percentages of macrophages in BAL cells did not differ. A significantly higher percent of phospho-ERK, phospho-p38 positive macrophages was observed in patients with SR asthma as compared with SS asthma. As shown in FIG. 7A, the percentage of phospho-p38 in SR asthma was (Mean±SE) 42.6%±16.3, as compared with 2.4%±4.5 in SS asthma (p=0.02), whereas percentage of phospho-ERK in SR asthma was 69.4%±16.3, as compared with 3.7%±3.5 in SS asthma (p=0.05).

In addition, BAL macrophages from SR asthmatics had a significantly greater mean fluorescence intensity (MFI) both for phospho-p38 and phospho-ERK staining as compared to BAL macrophages of SS asthmatics: MFI for phosphorylated p38 staining was 1304±120 vs. 798±98 (p=0.002), MFI for phosphorylated ERK staining was 935±71 vs. 461±84 P=0.009), in BAL macrophages for SR and SS asthma groups, respectively (FIG. 7B).

BAL macrophages from both asthma groups stained strongly for phospho-JNK. There was, however, no difference in phospho-JNK staining between SR and SS asthma groups.

Example 7

This example shows p38 phosphorylation in PBMC of asthmatics.

Data above showed that SR asthmatics had significantly increased numbers of BAL macrophages with phosphorylated ERK and p38 as compared with SS asthmatics. Next it was evaluated whether these differences in baseline MAPK phosphorylation were also be observed in the peripheral blood of SR asthmatics as compared to SS asthmatics. Western blot analyses were performed using whole protein extracts prepared from PBMC of 9 SR and 9 SS asthmatics.

Figure 8:
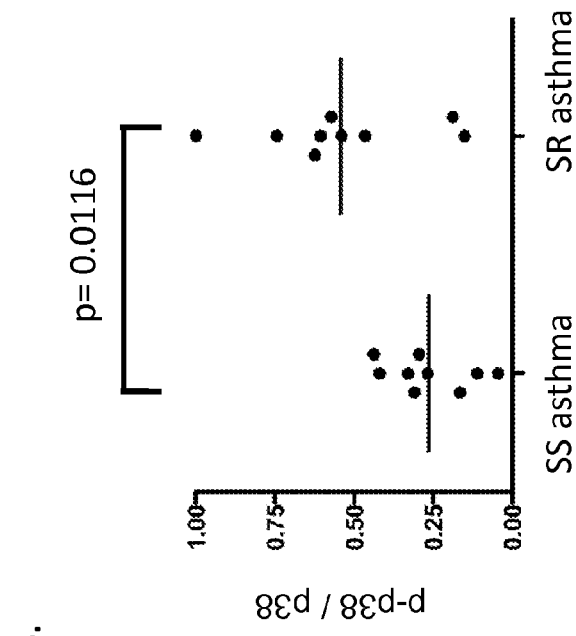
FIGS. 8A-8B show MAPKs phosphorylation in freshly isolated peripheral blood mononuclear cells (PBMC) of SS asthmatics and SR asthmatics as assessed by Western blot. PBMC cell lysates were prepared from nine subjects with SS asthma and nine subjects with SR asthma (FIG. 8A). 50 μg of protein from each patient PBMC cell extract was run on a 4-20% gradient gel and blots were probed with antibodies against phosphorylated forms of p38, ERK and JNK/SAPK. Membranes were stripped and re-probed with their total p38, ERK and JNK/SAPK, respectively. Hsp90 detection was used to monitor protein loading. Densitometry values of phosphorylated form of p38 to total p38 in PBMC of SR and SS asthmatics (FIG. 8B).
Figure 8:
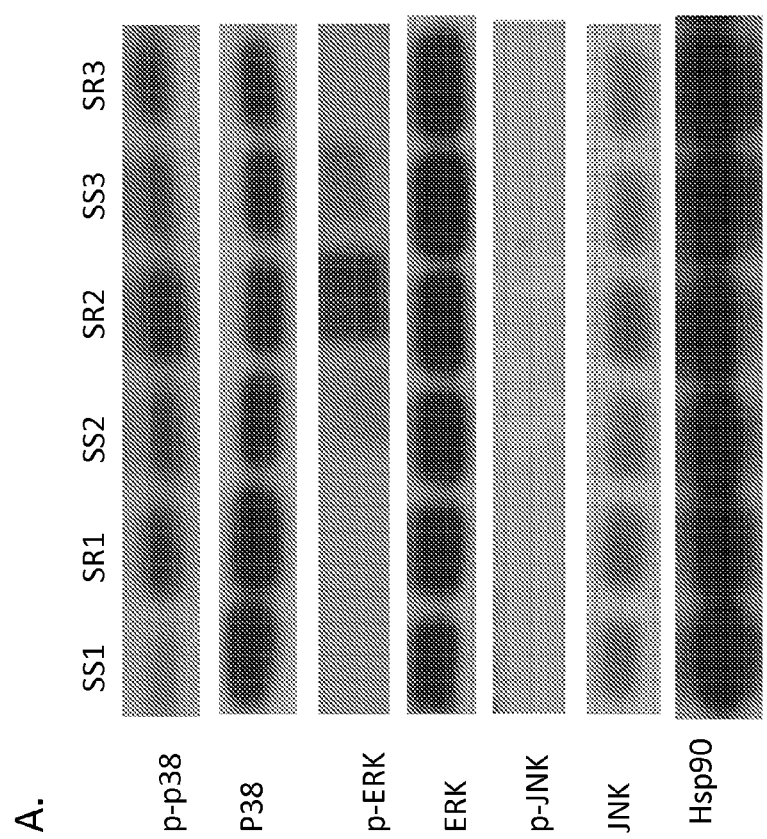

The presence of the activated form of p38 (p-p38) was observed in PBMC of all subjects with asthma (FIG. 8A). Moreover, significantly increased phosphorylation of p38 MAPK was detected in PBMC extracts from SR asthmatics compared with SS asthmatics (p<0.0116). The expression of total p38 in cells of two groups of asthmatics was similar.

In contrast, phosphorylated ERK was found only in one SR asthma subject out of 18 asthmatics tested. No JNK phosphorylation was detected in PBMC extracts from 18 asthmatics examined.

Figure 10:
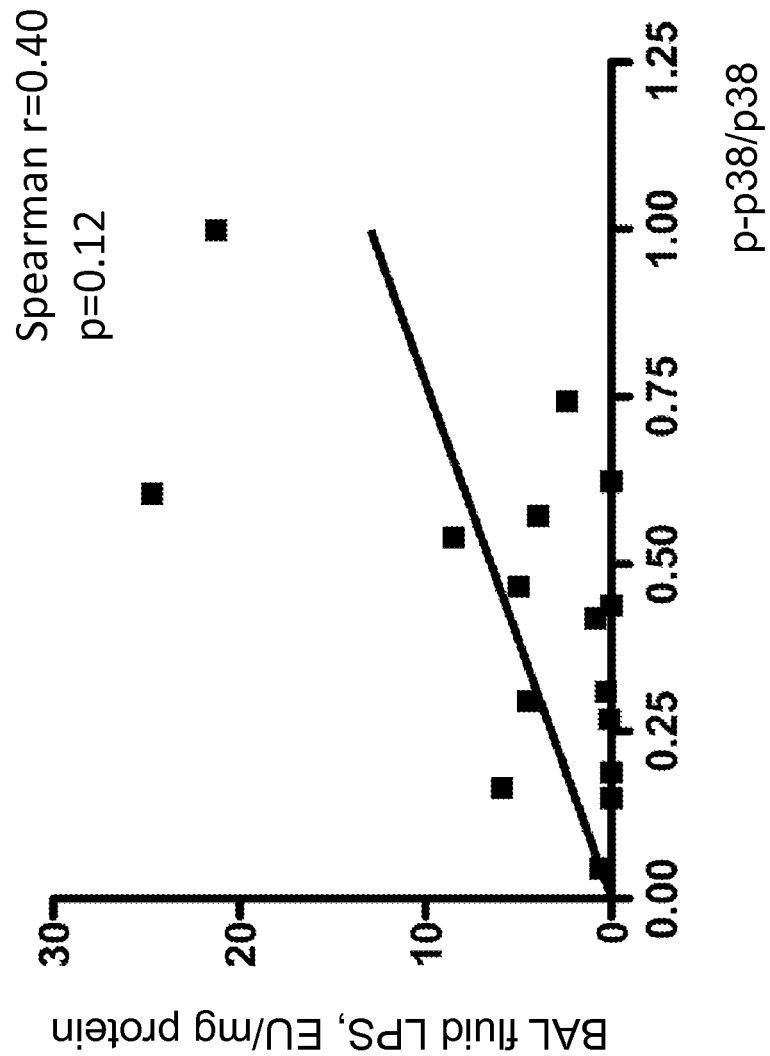
FIG. 10 shows the correlation between BAL fluid LPS levels and p38 phosphorylation in the PBMC of asthma patients as assessed by Western blot.

Of interest, a trend for positive correlation between the level p38 of phosphorylation in asthmatic PBMC and BAL fluid LPS levels in these patients was observed (Spearman ρ=0.40, p=0.12) (FIG. 10).

Example 8

This example demonstrates increased p38 phosphorylation in peripheral blood CD14$^+$ of SR asthmatics.

The inventors further determined what specific subsets of PBMC contribute to the increased p38 phosphorylation in PBMC of SR asthmatics. At the same time, ERK and JNK activation in PBMC was evaluated, as it was possible that activation of these kinases was only present in specific rare cell subsets in PBMC and therefore could not be detected by Western blot analysis using the PBMC extracts.

To do this, p38, ERK and JNK phosphorylation was analyzed by multiparameter flow-cytometry using whole blood from asthmatics. p-MAPK was detected in five different subsets of PBMC, i.e. CD4+ and CD8+ T cells, B cells, NK cells and monocytes. The inventors discovered that there were a significantly stronger signal for activated p38 in CD14$^+$ monocytes from SR than SS asthmatics (p=0.018), whereas no difference in phosphorylation of ERK, JNK in CD14$^+$ cells from both groups of asthmatics was observed. In addition, no significant difference in phosphorylated p38, ERK, JNK was detected in CD4$^+$, CD8$^+$ T cells, B cells and NK cells from SR vs. SS asthmatics.

Example 9

This example provides evidence for p38 pathway activation in the cells from SR asthmatics.

To provide support for activation of p38 signaling pathway in the cells of SR asthmatics the inventors evaluated phosphorylation of mitogen- and stress-activated protein kinase 1 (p-MSK1), kinase directly downstream of p38. MSK1 phosphorylation was examined by Western blot using the same cell lysates prepared to assess p38 phosphorylation in the study subjects. The levels of MSK1 phosphorylation was found to be significantly higher in PBMC lysates from SR asthmatics as compared to SS asthmatics (FIG. 9A, 9B), p<0.001.

Figure 9:
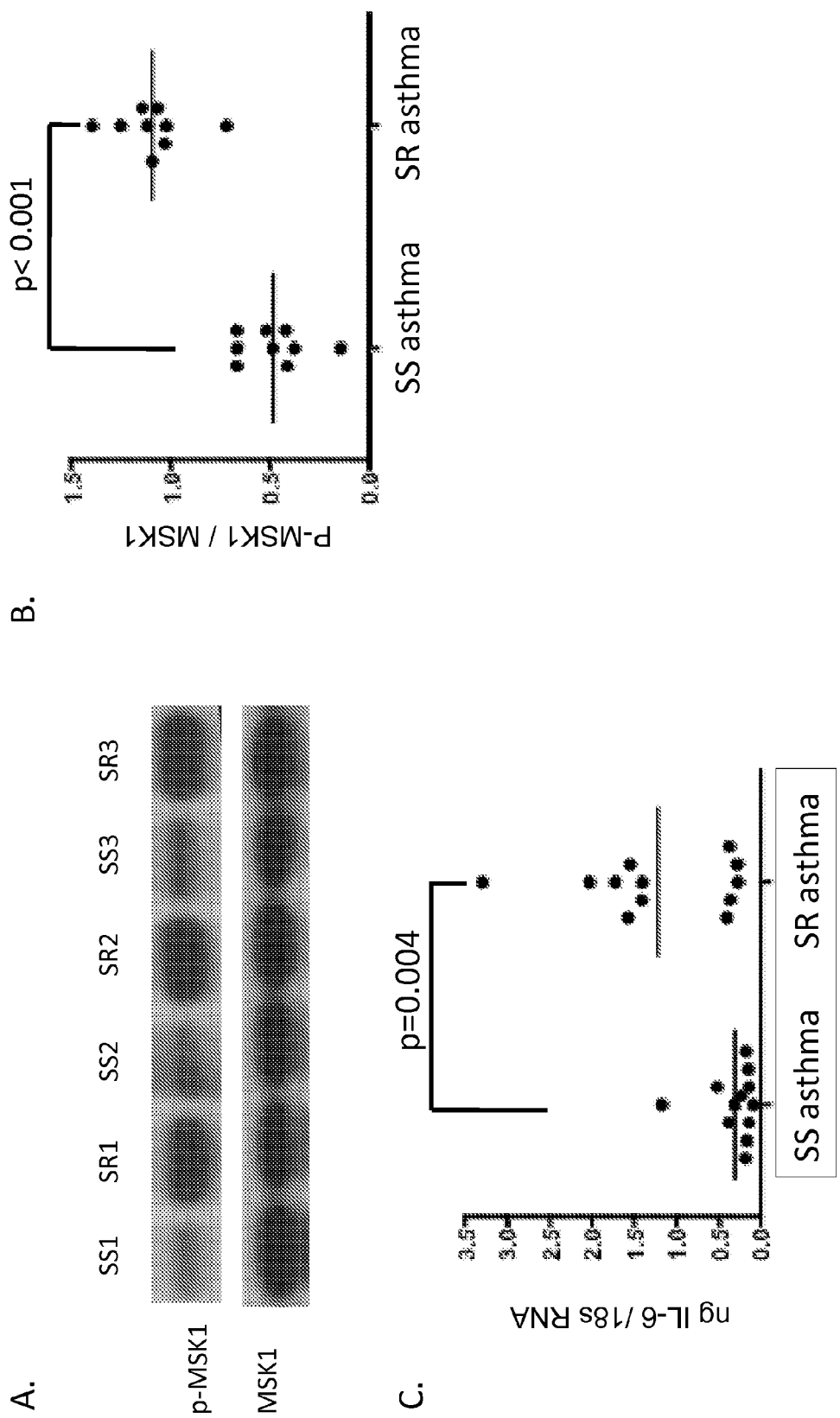
FIGS. 9A-9C show activation of the p38 pathway in the cells of SR asthmatics. SR asthmatics have significantly elevated p-MSK1 (Mitogen and Stress-Activated Protein Kinase 1) levels as compared to SS asthma patients (FIG. 9A). Representative Western blot results of p-MSK1 and MSK1 in PBMC are shown. PBMC protein lysates prepared to assess p38 phosphorylation as in FIG. 8A-8B, were examined for p-MSK1 expression. Densitometric values of phosphorylated form of MSK1 to total MSK1 in PBMC of SR and SS asthmatics (FIG. 9B). PBMC from SR asthmatics have significantly higher levels of IL-6 mRNA as compared to SS asthma patients as shown by real time PCR (FIG. 9C).

Activated p38 regulates cytokine production by the cells. IL-6 mRNA expression by PBMC of SR and SS asthmatics patients in the study was evaluated. IL-6 mRNA levels were found to be significantly greater in the PBMC of SR asthmatics supporting evidence for p38 pathway activation in these cells (p=0.004) (FIG. 9C).

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

REFERENCES

1. National Asthma Education and Prevention Program (National Heart Lung and Blood Institute) Third Expert Panel on the Management of Asthma., National Center for Biotechnology Information (U.S.). Expert Panel report 3 guidelines for the diagnosis and management of asthma. In: NIH publication no 07-4051. Bethesda, Md.: National Institutes of Health National Heart Lung and Blood Institute; 2007.
2. Global strategy for asthma management and prevention 2009 (update): Global Initiative for Asthma; 2009.
3. Malmstrom K, Rodriguez-Gomez G, Guerra J, et al. Oral montelukast, inhaled beclomethasone, and placebo for chronic asthma. A randomized, controlled trial. Montelukast/Beclomethasone Study Group. Ann Intern Med 1999; 130:487-95.
4. Martin R J, Szefler S J, King T S, et al. The Predicting Response to Inhaled Corticosteroid Efficacy (PRICE) trial. J Allergy Clin Immunol 2007; 119:73-80.
5. Barnes P J, Adcock I M. Glucocorticoid resistance in inflammatory diseases. Lancet 2009; 373:1905-17.
6. Leung D Y, Bloom J W. Update on glucocorticoid action and resistance. J Allergy Clin Immunol 2003; 111:3-22; quiz 3.
7. Leung D Y, Martin R J, Szefler S J, et al. Dysregulation of interleukin 4, interleukin 5, and interferon gamma gene expression in steroid-resistant asthma. J Exp Med 1995; 181:33-40.
8. Goleva E, Hauk P J, Boguniewicz J, Martin R J, Leung D Y. Airway remodeling and lack of bronchodilator response in steroid-resistant asthma. J Allergy Clin Immunol 2007; 120:1065-72.
9. Drazen J M. Asthma: the paradox of heterogeneity. J Allergy Clin Immunol 2012; 129:1200-1.
10. Hilty M, Burke C, Pedro H, et al. Disordered microbial communities in asthmatic airways. PLoS One 2010; 5:e8578.
11. Huang Y J, Nelson C E, Brodie E L, et al. Airway microbiota and bronchial hyperresponsiveness in patients with suboptimally controlled asthma. J Allergy Clin Immunol 2011; 127:372-81 e1-3.
12. Goleva E, Li L B, Eves P T, Strand M J, Martin R J, Leung D Y. Increased glucocorticoid receptor beta alters steroid response in glucocorticoid-insensitive asthma. Am J Respir Crit Care Med 2006; 173:607-16.
13. Sher E R, Leung D Y, Surs W, et al. Steroid-resistant asthma. Cellular mechanisms contributing to inadequate response to glucocorticoid therapy. J Clin Invest 1994; 93:33-9.
14. Hamid Q A, Wenzel S E, Hauk P J, et al. Increased glucocorticoid receptor beta in airway cells of glucocorticoid-insensitive asthma. Am J Respir Crit Care Med 1999; 159:1600-4.
15. Summary and recommendations of a workshop on the investigative use of fiberoptic bronchoscopy and bronchoalveolar lavage in asthmatics. Am Rev Respir Dis 1985; 132:180-2.
16. Guidelines for fiberoptic bronchoscopy in adults. American Thoracic Society. Medical Section of the American Lung Association. Am Rev Respir Dis 1987; 136:1066.
17. Busse W W, Wanner A, Adams K, et al. Investigative bronchoprovocation and bronchoscopy in airway diseases. Am J Respir Crit Care Med 2005; 172:807-16.
18. Goleva E, Hauk P J, Hall C F, et al. Corticosteroid-resistant asthma is associated with classical antimicrobial activation of airway macrophages. J Allergy Clin Immunol 2008; 122:550-9.
19. Magurran A E. Measuring Biological Diversity: Wiley; 2003.
20. Jost L. Partitioning diversity into independent alpha and beta components. Ecology 2007; 88:2427-39.
21. Akira S, Takeda K. Toll-like receptor signalling. Nat Rev Immunol 2004; 4:499-511.
22. Liew F Y, Xu D, Brint E K, O'Neill L A. Negative regulation of toll-like receptor-mediated immune responses. Nat Rev Immunol 2005; 5:446-58.
23. Raetz C R, Whitfield C. Lipopolysaccharide endotoxins Annu Rev Biochem 2002; 71:635-700.
24. Raetz C R, Reynolds C M, Trent M S, Bishop R E. Lipid A modification systems in gram-negative bacteria. Annu Rev Biochem 2007; 76:295-329.
25. Netea M G, van Deuren M, Kullberg B J, Cavaillon J M, Van der Meer J W. Does the shape of lipid A determine the interaction of LPS with Toll-like receptors? Trends Immunol 2002; 23:135-9.
26. Miller S I, Ernst R K, Bader M W. LPS, TLR4 and infectious disease diversity. Nat Rev Microbiol 2005; 3:36-46.
27. Erridge C, Bennett-Guerrero E, Poxton I R. Structure and function of lipopolysaccharides. Microbes Infect 2002; 4:837-51.
28. Park B S, Song D H, Kim H M, Choi B S, Lee H, Lee J O. The structural basis of lipopolysaccharide recognition by the TLR4-MD-2 complex. Nature 2009; 458: 1191-5.

29. Hashimoto M, Asai Y, Tamai R, Jinno T, Umatani K, Ogawa T. Chemical structure and immunobiological activity of lipid A from Prevotella intermedia ATCC 25611 lipopolysaccharide. FEBS Lett 2003; 543:98-102.
30. Larsen J M, Steen-Jensen D B, Laursen J M, et al. Divergent pro-inflammatory profile of human dendritic cells in response to commensal and pathogenic bacteria associated with the airway microbiota. PLoS One 2012; 7:e31976.
31. Kong H H, Oh J, Deming C, et al. Temporal shifts in the skin microbiome associated with disease flares and treatment in children with atopic dermatitis. Genome Res 2012; 22:850-9.
32. Nadkarni M A, Martin F E, Jacques N A, Hunter N. Determination of bacterial load by real-time PCR using a broad-range (universal) probe and primers set. Microbiology 2002; 148:257-66.
33. Mourani P M, Harris J K, Sontag M K, Robertson C E, Abman S H. Molecular identification of bacteria in tracheal aspirate fluid from mechanically ventilated preterm infants. PLoS One 2011; 6:e25959.
34. Hamady M, Walker J J, Harris J K, Gold N J, Knight R. Error-correcting barcoded primers for pyrosequencing hundreds of samples in multiplex. Nat Methods 2008; 5:235-7.
35. Harris J K, Sahl J W, Castoe T A, Wagner B D, Pollock D D, Spear J R. Comparison of normalization methods for construction of large, multiplex amplicon pools for next-generation sequencing. Appl Environ Microbiol 2010; 76:3863-8.
36. Frank D N. BARCRAWL and BARTAB: software tools for the design and implementation of barcoded primers for highly multiplexed DNA sequencing. BMC Bioinformatics 2009; 10:362.
37. Nawrocki E P, Kolbe D L, Eddy S R. Infernal 1.0: inference of RNA alignments. Bioinformatics 2009; 25:1335-7.
38. Haas B J, Gevers D, Earl A M, et al. Chimeric 16S rRNA sequence formation and detection in Sanger and 454-pyrosequenced PCR amplicons. Genome Res 2011; 21:494-504.
39. Wang Q, Garrity G M, Tiedje J M, Cole J R. Naive Bayesian classifier for rapid assignment of rRNA sequences into the new bacterial taxonomy. Appl Environ Microbiol 2007; 73:5261-7.
40. Pruesse E, Quast C, Knittel K, et al. SILVA: a comprehensive online resource for quality checked and aligned ribosomal RNA sequence data compatible with ARB. Nucleic Acids Res 2007; 35:7188-96.
41. Wagner B D, Robertson C E, Harris J K. Application of two-part statistics for comparison of sequence variant counts. PLoS One 2011; 6:e20296.
42. Zhang Y, Leung D Y M, Richers B N, et al. Vitamin D inhibits monocyte/macrophage pro-inflammatory cytokine production by targeting mitogen-activated protein kinase phosphatase 1 J Immunol 2012, in press.
43. Goleva E, Jackson L P, Gleason M, Leung D Y. Usefulness of PBMCs to predict clinical response to corticosteroids in asthmatic patients. J Allergy Clin Immunol 2012; 129:687-93 e1.
44. Li L B, Goleva E, Hall C F, Ou L S, Leung D Y. Superantigen-induced corticosteroid resistance of human T cells occurs through activation of the mitogen-activated protein kinase kinase/extracellular signal-regulated kinase (MEK-ERK) pathway. J Allergy Clin Immunol 2004; 114:1059-69.
45. Zhang Y, Leung D Y, Nordeen S K, Goleva E. Estrogen inhibits glucocorticoid action via protein phosphatase 5 (P P5)-mediated glucocorticoid receptor dephosphorylation. J Biol Chem 2009; 284:24542-52.
46. Ivanov, I I, Littman D R. Modulation of immune homeostasis by commensal bacteria. Curr Opin Microbiol 2011; 14:106-14.
47. Artis D. Epithelial-cell recognition of commensal bacteria and maintenance of immune homeostasis in the gut. Nat Rev Immunol 2008; 8:411-20.
48. Lai Y, Di Nardo A, Nakatsuji T, et al. Commensal bacteria regulate Toll-like receptor 3-dependent inflammation after skin injury. Nat Med 2009; 15:1377-82.
49. Abreu N A, Nagalingam N A, Song Y, et al. Sinus Microbiome Diversity Depletion and *Corynebacterium tuberculostearicum* Enrichment Mediates Rhinosinusitis. Sci Transl Med 2012; 4:151ra24.
50. Charlson E S, Bittinger K, Haas A R, et al. Topographical continuity of bacterial populations in the healthy human respiratory tract. Am J Respir Crit Care Med 2011; 184:957-63.
51. Grice E A, Segre J A. The human microbiome: our second genome. Annu Rev Genomics Hum Genet 2012; 13:151-70.
52. McManus R. Mechanisms of steroid action and resistance in inflammation and disease. *J Endocrinol* 2003; 178:1-4.
53. Leung D Y, Bloom J W. Update on glucocorticoid action and resistance. *J Allergy Clin Immunol* 2003; 111:3-22; quiz 23.
54. Althuis M D, Sexton M, Prybylski D. Cigarette smoking and asthma symptom severity among adult asthmatics. *J Asthma* 1999; 36:257-264.
55. Sutherland E R, Goleva E, Jackson L P, Stevens A D, Leung D Y. Vitamin d levels, lung function, and steroid response in adult asthma. *Am J Respir Crit Care Med* 2010; 181:699-704.
56. Yang M, Kumar R K, Foster P S. Pathogenesis of steroid-resistant airway hyperresponsiveness: Interaction between ifn-gamma and tlr4/myd88 pathways. *J Immunol* 2009; 182:5107-5115.
57. Goleva E, Hauk P J, Hall C F, Liu A H, Riches D W, Martin R J, Leung D Y. Corticosteroid-resistant asthma is associated with classical antimicrobial activation of airway macrophages. *J Allergy Clin Immunol* 2008; 122: 550-559 e553.
58. Bhaysar P, Hew M, Khorasani N, Torrego A, Barnes P J, Adcock I, Chung K F. Relative corticosteroid insensitivity of alveolar macrophages in severe asthma compared with non-severe asthma. *Thorax* 2008; 63:784-790.
59. Rossol M, Heine H, Meusch U, Quandt D, Klein C, Sweet M J, Hauschildt S. Lps-induced cytokine production in human monocytes and macrophages. *Crit Rev Immunol* 2011; 31:379-446.
60. Liu A H. Something old, something new: Indoor endotoxin, allergens and asthma. *Paediatr Respir Rev* 2004; 5 Suppl A:S65-71.
61. Michel O, Kips J, Duchateau J, Vertongen F, Robert L, Collet H, Pauwels R, Sergysels R. Severity of asthma is related to endotoxin in house dust. *Am J Respir Crit Care Med* 1996; 154:1641-1646.
62. Rizzo M C, Naspitz C K, Fernandez-Caldas E, Lockey R F, Mimica I, Sole D. Endotoxin exposure and symptoms in asthmatic children. *Pediatr Allergy Immunol* 1997; 8:121-126.
62. Gioannini T L, Teghanemt A, Zhang D, Prohinar P, Levis E N, Munford R S, Weiss J P. Endotoxin-binding proteins 62. modulate the susceptibility of bacterial endotoxin to deacylation by acyloxyacyl hydrolase. *J Biol Chem* 2007; 282:7877-7884.
63. Fitzgerald K A, Rowe D C, Barnes B J, Caffrey D R, Visintin A, Latz E, Monks B, Pitha P M, Golenbock D T. Lps-tlr4 signaling to irf-3/7 and nf-kappab involves the toll adapters tram and trif. *J Exp Med* 2003; 198:1043-1055.
64. Guha M, Mackman N. Lps induction of gene expression in human monocytes. *Cell Signal* 2001; 13:85-94.
65. Carter A B, Monick M M, Hunninghake G W. Both erk and p38 kinases are necessary for cytokine gene transcription. *Am J Respir Cell Mol Biol* 1999; 20:751-758.
66. Lim W, Gee K, Mishra S, Kumar A. Regulation of b7.1 costimulatory molecule is mediated by the ifn regulatory factor-7 through the activation of jnk in lipopolysaccharide-stimulated human monocytic cells. *J Immunol* 2005; 175:5690-5700.
67. Rawadi G, Garcia J, Lemercier B, Roman-Roman S. Signal transduction pathways involved in the activation of nf-kappa b, ap-1, and c-fos by mycoplasma fermentans membrane lipoproteins in macrophages. *J Immunol* 1999; 162:2193-2203.
68. Oeckinghaus A, Hayden M S, Ghosh S. Crosstalk in nf-kappab signaling pathways. *Nat Immunol* 2011; 12:695-708.
69. Liu Y, Shepherd E G, Nelin L D. Mapk phosphatases—regulating the immune response. *Nat Rev Immunol* 2007; 7:202-212.
70. Lasa M, Abraham S M, Boucheron C, Saklatvala J, Clark A R. Dexamethasone causes sustained expression of mitogen-activated protein kinase (mapk) phosphatase 1 and phosphatase-mediated inhibition of mapk p38. *Mol Cell Biol* 2002; 22:7802-7811.
71. Ismaili N, Garabedian M J. Modulation of glucocorticoid receptor function via phosphorylation. *Ann N Y Acad Sci* 2004; 1024:86-101.
72. Galliher-Beckley A J, Cidlowski J A. Emerging roles of glucocorticoid receptor phosphorylation in modulating glucocorticoid hormone action in health and disease. *IUBMB Life* 2009; 61:979-986.
73. Dealt M, Clifton A D, Lucocq L M, Alessi D R. Mitogen- and stress-activated protein kinase-1 (msk1) is directly activated by mapk and sapk2/p38, and may mediate activation of creb. *EMBO J* 1998; 17:4426-4441.
74. Chung K F. P38 mitogen-activated protein kinase pathways in asthma and copd. *Chest* 2011; 139:1470-1479.
75. Liu W, Tundwal K, Liang Q, Goplen N, Rozario S, Quayum N, Gorska M, Wenzel S, Balzar S, Alam R. Establishment of extracellular signal-regulated kinase 1/2 bistability and sustained activation through sprouty 2 and its relevance for epithelial function. *Mol Cell Biol* 2010; 30:1783-1799.
76. Shan L, Redhu N S, Saleh A, Halayko A J, Chakir J, Gounni A S. Thymic stromal lymphopoietin receptor-mediated il-6 and cc/cxc chemokines expression in human airway smooth muscle cells: Role of mapks (erkl/2, p38, and jnk) and stat3 pathways. *J Immunol* 2010; 184:7134-7143.
77. Liu W, Liang Q, Balzar S, Wenzel S, Gorska M, Alam R. Cell-specific activation profile of extracellular signal-regulated kinase 1/2, jun n-terminal kinase, and p38 mitogen-activated protein kinases in asthmatic airways. *J Allergy Clin Immunol* 2008; 121:893-902 e892.
78. Goleva E, Li L B, Leung D Y. Ifn-gamma reverses il-2- and il-4-mediated t-cell steroid resistance. *Am J Respir Cell Mol Biol* 2009; 40:223-230.
79. Bhavsar P, Khorasani N, Hew M, Johnson M, Chung K F. Effect of p38 mapk inhibition on corticosteroid suppression of cytokine release in severe asthma. *Eur Respir J* 2010; 35:750-756.
80. Vermeulen L, De Wilde G, Van Damme P, Vanden Berghe W, Haegeman G. Transcriptional activation of the nf-kappab p65 subunit by mitogen- and stress-activated protein kinase-1 (msk1). *EMBO J* 2003; 22:1313-1324.
81. Beck I M, Vanden Berghe W, Gerlo S, Bougarne N, Vermeulen L, De Bosscher K, Haegeman G. Glucocorticoids and mitogen- and stress-activated protein kinase 1 inhibitors: Possible partners in the combat against inflammation. *Biochem Pharmacol* 2009; 77:1194-1205.
82. Beck I M, Vanden Berghe W, Vermeulen L, Bougarne N, Vander Cruyssen B, Haegeman G, De Bosscher K. Altered subcellular distribution of msk1 induced by glucocorticoids contributes to nf-kappab inhibition. EMBO J 2008; 27:1682-1693.

What is claimed is:

1. A method to identify and treat a subject having an inflammatory disease resistant to corticosteroid treatment, wherein the disease is asthma, said method comprising
   a. obtaining a biological sample from the subject;
   b. determining the level of phosphorylated transforming growth factor β-activated kinase 1 (p-TAK1) in a biological sample from the subject;
   c. identifying the subject as having an inflammatory disease resistant to corticosteroid treatment when an elevated level of p-TAK1 compared to a control level of p-TAK1 is determined; and
   d. administering an effective amount of a compound that inhibits transforming growth factor beta associated kinase-1 (TAK1) activity, wherein the compound is (5Z)-7-oxozeaenol.

2. The method of claim 1, wherein the asthma is associated with a chronic obstructive disease of the airways.

3. The method of claim 1, wherein the asthma is associated with viral induced inflammation.

4. The method of claim 1, wherein the asthma is triggered by the subject's exposure to environmental conditions selected from the group consisting of second hand smoke, primary tobacco smoke, and an allergen.

5. The method of claim 1 wherein the biological sample is selected from the group consisting of serum, plasma, blood, urine, sputum, peripheral blood mononuclear cells (PBMCs), epithelial cells, sinus tissue, and nasal tissue.

6. The method of claim 1 wherein the subject is human.

7. The method of claim 1, wherein the elevated level of p-TKA1 is determined to be at least two-fold greater than the control level of p-TAK1.

* * * * *